US010272084B2

(12) United States Patent
Kavelaars et al.

(10) Patent No.: US 10,272,084 B2
(45) Date of Patent: Apr. 30, 2019

(54) HISTONE DEACETYLASE 6 SELECTIVE INHIBITORS FOR THE TREATMENT OF CISPLATIN-INDUCED PERIPHERAL NEUROPATHY

(71) Applicants: REGENACY PHARMACEUTICALS, LLC, Boston, MA (US); Board of Regents, The University of Texas System, Austin, TX (US)

(72) Inventors: Annemieke Kavelaars, Houston, TX (US); Cobi J. Heijnen, Houston, TX (US); Karen Krukowski, San Francisco, CA (US); Matthew B. Jarpe, Quincy, MA (US)

(73) Assignees: Regenacy Pharmaceuticals, LLC, Waltham, MA (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/170,335

(22) Filed: Jun. 1, 2016

(65) Prior Publication Data
US 2016/0346279 A1 Dec. 1, 2016

Related U.S. Application Data

(60) Provisional application No. 62/169,528, filed on Jun. 1, 2015.

(51) Int. Cl.
*A61K 31/505* (2006.01)
*A61K 33/24* (2019.01)

(52) U.S. Cl.
CPC ............ *A61K 31/505* (2013.01); *A61K 33/24* (2013.01)

(58) Field of Classification Search
CPC .................................................. A61K 31/505
See application file for complete search history.

(56) References Cited

U.S. PATENT DOCUMENTS

| | | | |
|---|---|---|---|
| 3,549,633 A | 12/1970 | Grabowski et al. | |
| 6,777,217 B1 | 8/2004 | Schreiber et al. | |
| 7,244,853 B2 | 7/2007 | Schreiber et al. | |
| 7,250,504 B2 | 7/2007 | Grozinger et al. | |
| 7,994,362 B2 | 8/2011 | Schreiber et al. | |
| 8,148,526 B1 | 4/2012 | van Duzer et al. | |
| 8,614,223 B2 | 12/2013 | van Duzer et al. | |
| 9,409,890 B2 | 8/2016 | van Duzer et al. | |
| 2004/0266769 A1 | 12/2004 | Bressi et al. | |
| 2006/0239909 A1 | 10/2006 | Anderson et al. | |
| 2007/0093413 A1 | 4/2007 | Schreiber et al. | |
| 2007/0149495 A1 | 6/2007 | Bressi et al. | |
| 2008/0207590 A1 | 8/2008 | Deziel et al. | |
| 2009/0023786 A1 | 1/2009 | Miller et al. | |
| 2009/0209590 A1 | 8/2009 | Mazitschek et al. | |
| 2009/0305384 A1 | 12/2009 | Grozinger et al. | |
| 2009/0312363 A1 | 12/2009 | Bradner et al. | |
| 2010/0137196 A1 | 6/2010 | Schreiber et al. | |
| 2010/0152254 A1 | 6/2010 | Bialer et al. | |
| 2010/0168463 A1 | 7/2010 | Hirata et al. | |
| 2011/0218154 A1 | 9/2011 | Schreiber et al. | |
| 2011/0300134 A1 | 12/2011 | van Duzer et al. | |
| 2013/0225543 A1 | 8/2013 | Jones et al. | |
| 2014/0357512 A1 | 12/2014 | Jones et al. | |
| 2015/0239869 A1* | 8/2015 | Mazitschek | C07D 405/12 514/275 |
| 2015/0250786 A1 | 9/2015 | Berton et al. | |
| 2016/0158231 A1 | 6/2016 | Jarpe et al. | |

FOREIGN PATENT DOCUMENTS

| | | |
|---|---|---|
| EP | 2 524 918 A1 | 11/2012 |
| WO | 2003/037869 A1 | 5/2003 |
| WO | 2003/076401 A1 | 9/2003 |
| WO | 2003/076430 A1 | 9/2003 |
| WO | 2004/052869 A1 | 6/2004 |
| WO | 2005/012261 A1 | 2/2005 |
| WO | 2005/028447 A1 | 3/2005 |
| WO | 2005/030705 A1 | 4/2005 |
| WO | 2006/102557 A2 | 9/2006 |
| WO | 2006/123121 A1 | 11/2006 |
| WO | 2007/022638 A1 | 3/2007 |
| WO | 2007/091703 A2 | 8/2007 |
| WO | 2007/130429 A2 | 11/2007 |
| WO | 2008/055068 A2 | 5/2008 |
| WO | 2008/091349 A1 | 7/2008 |
| WO | 2009/137462 A1 | 11/2009 |
| WO | 2009/137503 A1 | 11/2009 |
| WO | 2010/009155 A2 | 1/2010 |
| WO | 2010/011296 A2 | 1/2010 |
| WO | 2010/080996 A1 | 7/2010 |
| WO | 2011/011186 A1 | 1/2011 |
| WO | 2011/019393 A2 | 2/2011 |
| WO | 2011/084991 A2 | 7/2011 |

(Continued)

OTHER PUBLICATIONS

Park et al. Ca Cancer J. Clin., 2013, vol. 63, pp. 419-437.*
Wang et al., European J. of Med. Chem., 2018, vol. 143, pp. 1406-1418.*
Angibaud et al. (2005) "Discovery of Pyrimidyl-5-hydroxamic acids as New Potent Histone Deacetylase Inhibitors," European Journal of Medicinal Chemistry. 40(6):597-606.
Brana et al. (2002) "Synthesis and biological evaluation of novel 2-(1H-imidazol-4-yl)cyclopropane carboxylic acids: key intermediates for H3 histamine receptor ligands," BioOrganic & Medicinal Chemistry Letter. 12(24):3561-3563.
Broxterman et al. (1992) "Synthesis of (optically active) sulfur-containing trifunctional amino acids by radical addition to (optically active) unsaturated amino acids," The Journal of Organic Chemistry. 57(23):6286-6294.
Butler et al. (2000) "Suberoylanilide Hydroxamic Acid, an Inhibitor of Histone Deactylase, Suppresses the Growth of Prostate Cancer Cells in Vitro and in Vivo," Cancer Research. 60:5165-5170.

(Continued)

*Primary Examiner* — Samira J Jean-Louis
(74) *Attorney, Agent, or Firm* — Brian C. Trinque; Lathrop Gage LLP

(57) ABSTRACT

Disclosed are methods for treating cisplatin-induced peripheral neuropathy in a subject in need thereof comprising administering to the subject a therapeutically effective amount of a histone deacetylase 6 selective inhibitor.

6 Claims, 16 Drawing Sheets

(56) References Cited

FOREIGN PATENT DOCUMENTS

| WO | 2012/018499 | A1 | 2/2012 |
| WO | 2012/045804 | A1 | 4/2012 |
| WO | 2014/059306 | A1 | 4/2014 |

OTHER PUBLICATIONS

Carey et al. (2006) "Histone deacetylase inhibitors: gathering pace," Current Opinion in Pharmacology. 6:369-375.
Chuang et al. (2009) "Multiple roles of HDAC inhibition in neurodegenerative conditions," Trends in Neurosciences. 32 (11):591-601.
Dallavalle et al. (2012) "Development and therapeutic impact of HDAC6-selective inhibitors," Biochemical Pharmacology. 84:756-765.
Elaut et al. (2007) "The Pharmaceutical Potential of Histone Deacetylase Inhibitors," Current Pharmaceutical Design. 13:2584-2620.
Foks et al. (1972) "Investigations on Pyrazine Derivatives Part II. Synthesis and Tuberculostatic Action of Some 6 Alkylaminopyrazine-2-carboxylic acids," Dissertationes Pharmaceuticae and Pharmacologicae. 24:(6)577-583.
Foks et al. (1974) "Studies on Pyrazine Derivatives," Pol. J. Pharmacol. Pharm. 26:537-543.
Haggarty et al. (2003) "Domain-selective Small-molecule Inhibitor of Histone Deacetylase 6 (HDAC6)-mediated Tubulin Deacetylation," Proc. Natl. Acad. Sci. USA. 100(8):4389-4394.
Jochems et al. (Nov. 6, 2013) "Antidepressant-Like Properties of Novel HDAC6-Selective Inhibitors with Improved Brain Bioavailability," Neuropsychopharmacology. 39(2):389-400.
Lane et al. (2009) "Histone deacetylase inhibitors in cancer therapy," J. Clin. Oncol. 27:5459-5468.
Neidle, Stephen: Ed. (2008) Cancer Drug Design and Discovery. Elsevier/Academic Press. pp. 427-431.
Pellicciari et al. (1996) "Synthesis and Pharmacological Characterization of All Sixteen Stereoisomers of 2-(2'-Carboxy-3'-phenylcyclopropyl)glycine. Focus on (2S,1'S,2'S,3'R)-2-(2'-Carboxy-3'-phenylcyclopropyl)glycine, a Novel and Selective Group II Metabotropic Glutamate Receptors Antagonist," Journal of Medicinal Chemistry. 39(11):2259-2269.
Rajak et al. (2011) "2,5-Disubstituted-1,3,4-oxadiazoles/thiadiazole as Surface Recognition Moiety: Design and Synthesis of Novel Hydroxamic acid Based Histone Deacetylase Inhibitors," Bioorganic & Medicinal Chemistry Letters. 21(19):5735-5738.
Walbrick et al.(1968) "A general method for synthesizing optically active 1,3-disubstituted allene hydrocarbons," The Journal of the American Chemical Society. 90(11):2895-2901.
Warner et al. (1992) "Electron demand in the transition state of the cyclopropylidene to allene ring opening," The Journal of Organic Chemistry. 57(23):6294-6300.
International Preliminary Report on Patentability corresponding to International Patent Application No. PCT/US2011/060791, dated Jul. 22, 2014.
International Search Report corresponding to International Patent Application No. PCT/US2011/021982, dated Oct. 12, 2011.
International Search Report with Written Opinion corresponding to International Patent Application No. PCT/US2011/060791, dated Mar. 5, 2014.
International Search Report with Written Opinion corresponding to International Patent Application No. PCT/US2015/063959, dated May 19, 2016.
Supplementary European Search Report corresponding to European Application No. 11840803.8, dated Mar. 5, 2014.

* cited by examiner

HISTONE DEACETYLASE 6 SELECTIVE INHIBITORS FOR THE TREATMENT OF CISPLATIN-INDUCED PERIPHERAL NEUROPATHY

RELATED APPLICATION

This application claims the benefit of U.S. Provisional Application Ser. No. 62/169,528, filed Jun. 1, 2015, the content of which is incorporated herein in its entirety.

BACKGROUND

Neurotoxic side-effects of chemotherapy, including pain and numbness in hands and feet, frequently lead to dose reduction. This chemotherapy-induced peripheral neuropathy (CIPN) often persists long into survivorship and negatively affects quality of life. There are no drugs available to prevent or treat CIPN, and underlying mechanisms are only partially understood. Only a few studies have studied chemotherapy-induced numbness because of lack of relevant animal models.

The high prevalence and incidence of CIPN along with the lack of effective treatments makes identification of therapeutics and understanding of mechanistic drivers of CIPN vital for improving quality of life in cancer patients and survivors. Accordingly, there remains a need to alleviate the symptoms of chemotherapy-induced peripheral neuropathy

SUMMARY

Provided herein are pharmaceutical compounds for the treatment of cisplatin-induced peripheral neuropathies in a subject in need thereof. Also provided herein are methods for treating a cisplatin-induced peripheral neuropathy in a subject in need thereof.

In a first aspect, provided herein are methods of treating cisplatin-induced peripheral neuropathy in a subject in need thereof comprising administering to the subject a therapeutically effective amount of a histone deacetylase 6 selective inhibitor, to thereby treat or prevent the cisplatin-induced peripheral neuropathy. In such an aspect, the histone deacetylase 6 selective inhibitor can be compound 001:

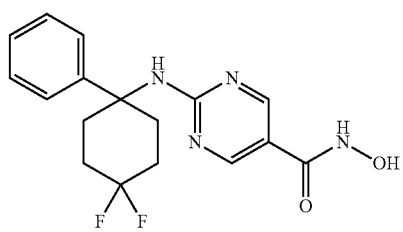

(001)

or a pharmaceutically acceptable salt thereof. The histone deacetylase 6 selective inhibitor can be co-administered with cisplatin, or administered before or after administering cisplatin. The cisplatin-induced peripheral neuropathy can exist in the subject prior to administering the histone deacetylase 6 selective inhibitor.

In a second aspect, provided herein is a method of treating cisplatin-induced peripheral neuropathy in a subject in need thereof comprising administering to the subject a therapeutically effective amount of compound 001:

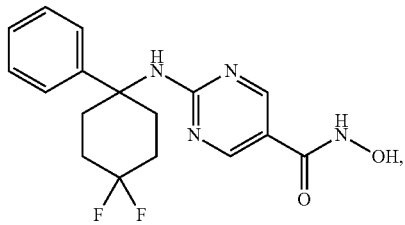

(001)

or a pharmaceutically acceptable salt thereof, to thereby treat the cisplatin-induced peripheral neuropathy. Compound 001 can be co-administered with cisplatin, or administered before or after administering cisplatin. The cisplatin-induced peripheral neuropathy can exist in the subject prior to administering the histone deacetylase 6 selective inhibitor.

In yet a third aspect, provided herein are methods of inhibiting cisplatin-induced astrocyte activation in a subject, comprising administering to the subject a therapeutically effective amount of a histone deacetylase 6 selective inhibitor to thereby inhibit astrocyte activation.

In a fourth aspect, provided herein are methods of inhibiting a decrease in cisplatin-induced neuronal mitochondrial transport comprising contacting a neuron with an effective amount of a histone deacetylase 6 selective inhibitor to thereby inhibit the decrease of cisplatin-induced neuronal mitochondrial transport.

In a fifth aspect, provided herein are methods of treating cisplatin-induced pain, comprising administering to a subject in need thereof an effective amount of a histone deacetylase 6 selective inhibitor to thereby treat the pain in the subject. The cisplatin-induced pain can exist in the subject prior to administering the histone deacetylase 6 selective inhibitor.

In a sixth aspect, provided herein are methods of treating cisplatin-induced numbness, comprising administering to a subject in need thereof an effective amount of a histone deacetylase 6 selective inhibitor to thereby treat the numbness in the subject. The cisplatin-induced numbness can exist in the subject prior to administering the histone deacetylase 6 selective inhibitor.

In any of the third through sixth aspects, the histone deacetylase 6 selective inhibitor can be compound 001:

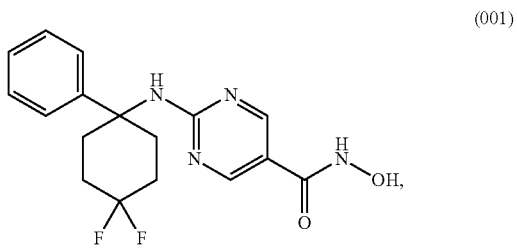 [SMILES: O=C(NO)c1cnc(NC2(c3ccccc3)CCC(F)(F)CC2)nc1]

(001)

or a pharmaceutically acceptable salt thereof.

In a seventh aspect, provided herein is a method for restoring the loss of intra-epidermal nerve fiber (IENF) in a subject, comprising administering to the subject an effective amount of a histone deacetylase 6 selective inhibitor.

In an embodiment of the seventh aspect, the loss of intra-epidermal nerve fiber is the result of administering cisplatin to the subject.

In another embodiment of the seventh aspect, the administration of the histone deacetylase 6 selective inhibitor to the subject occurs during or after administering cisplatin.

In yet another embodiment of the seventh aspect, the histone deacetylase 6 selective inhibitor can be compound 001:

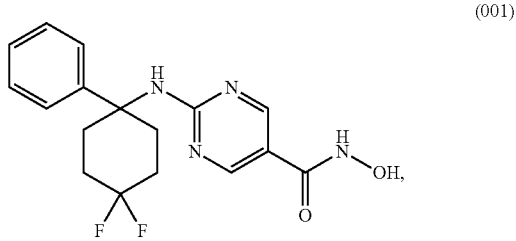 [SMILES: O=C(NO)c1cnc(NC2(c3ccccc3)CCC(F)(F)CC2)nc1]

(001)

or a pharmaceutically acceptable salt thereof.

Representative examples of immunofluorescence: (A) saline+vehicle (B) saline+compound 001 (C) cisplatin+vehicle (D) cisplatin+compound 001. (E) GFAP levels (area positive) in the spinal dorsal horn were quantified using Image J Analysis software, n=3-4 mice/group. Two-way ANOVA revealed a signification interaction ($p<0.05$). Tukey post-hoc analysis revealed significant differences between groups: *$p<0.05$. Scale bar=20 μm; 40× magnification.

Figure 6:
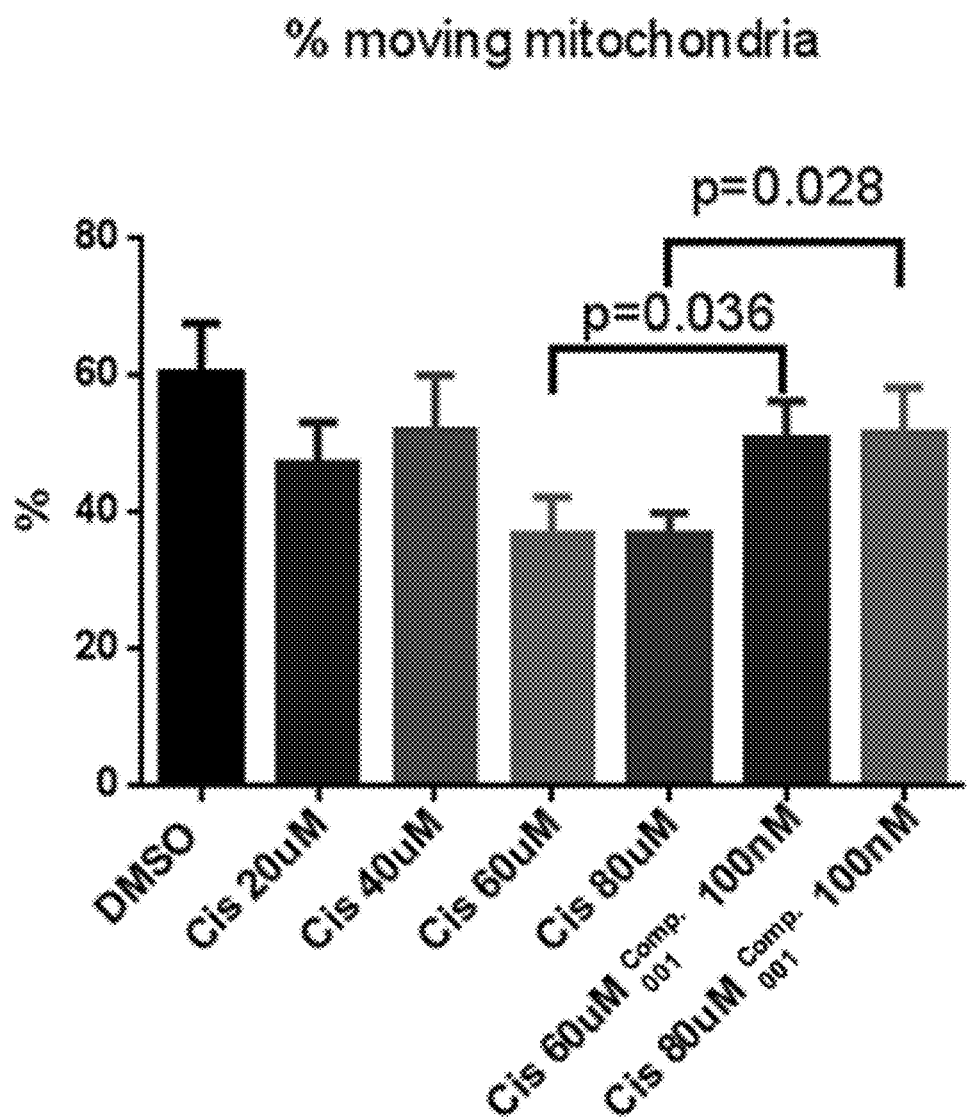

FIG. 6 shows that compound 001 prevents cisplatin-induced decreases in mitochondrial transport in vitro. Mitochondrial transport was determined with rat DRG neuron cultures in vitro.

Figure 7A:
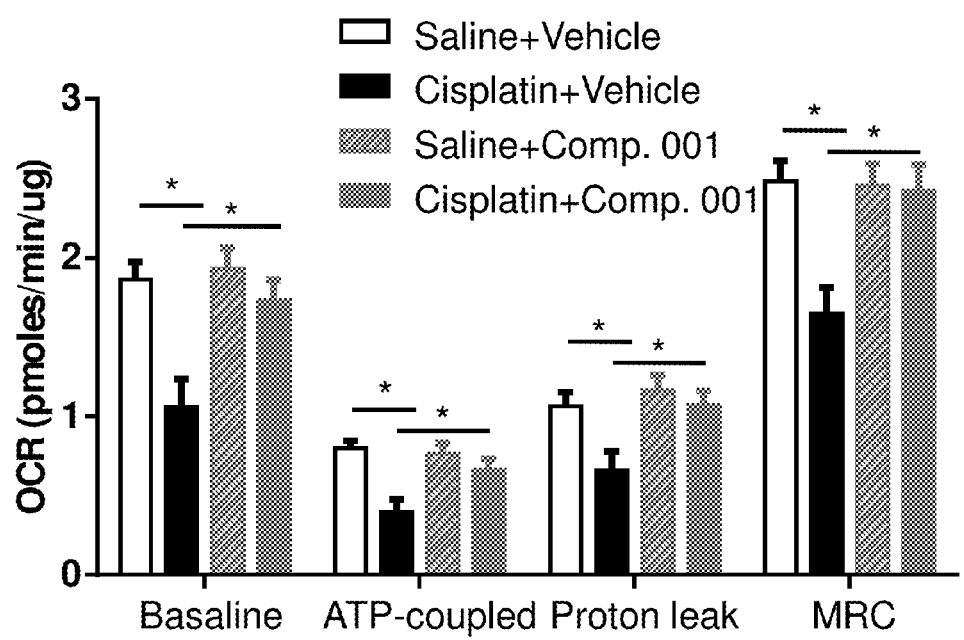

FIG. 7A shows mitochondrial bioenergetics in tibial nerves from mice that had received 2 rounds of cisplatin treatment and 11 injections of compound 001. Two-way ANOVA revealed a signification interaction ($p<0.05$) and treatment (compound 001) effect ($p<0.05$) for baseline respiration, ATP-coupled respiration, proton leak and maximal respiratory capacity. Tukey post-hoc analysis revealed significant differences between groups: *$p<0.05$.

Figure 7B:
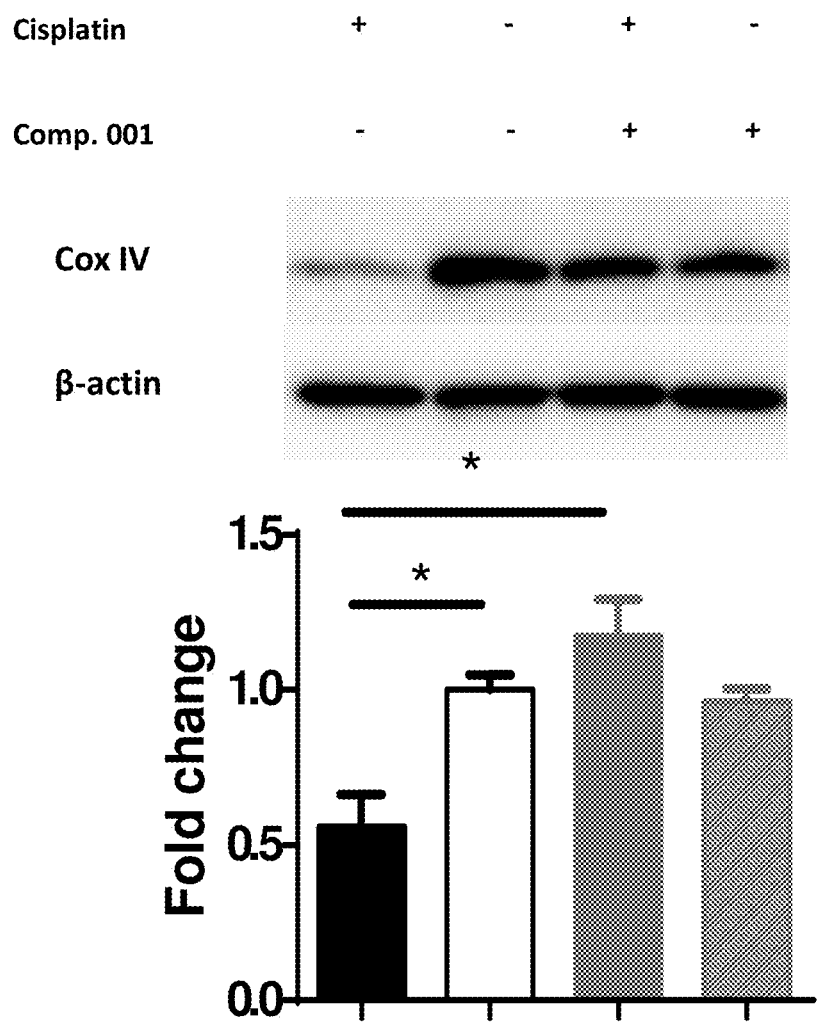

FIG. 7B shows tibal nerves retrieved from the XF-analysis were used for Western blot analysis of mitochondrial marker protein Cox IV, n=6-8 mice/group. Two-way ANOVA revealed a significant treatment (compound 001) effect ($p<0.05$). Tukey post-hoc analysis revealed significant differences between groups: *$p<0.05$.

Figure 7C:
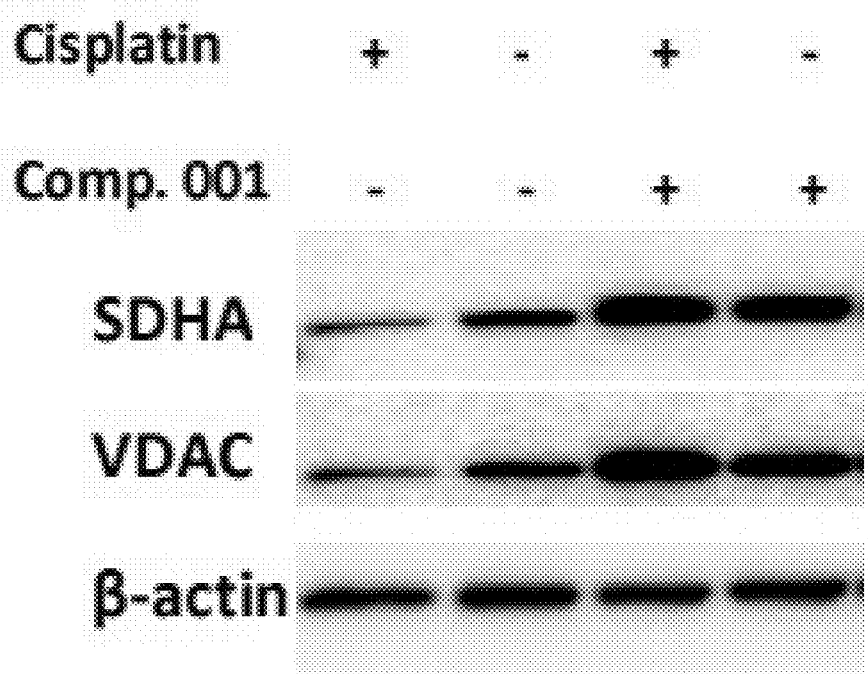

FIG. 7C shows tibial nerves were used for Western blot analysis of additional mitochondrial marker proteins SDHA and VDAC.

Figure 8:
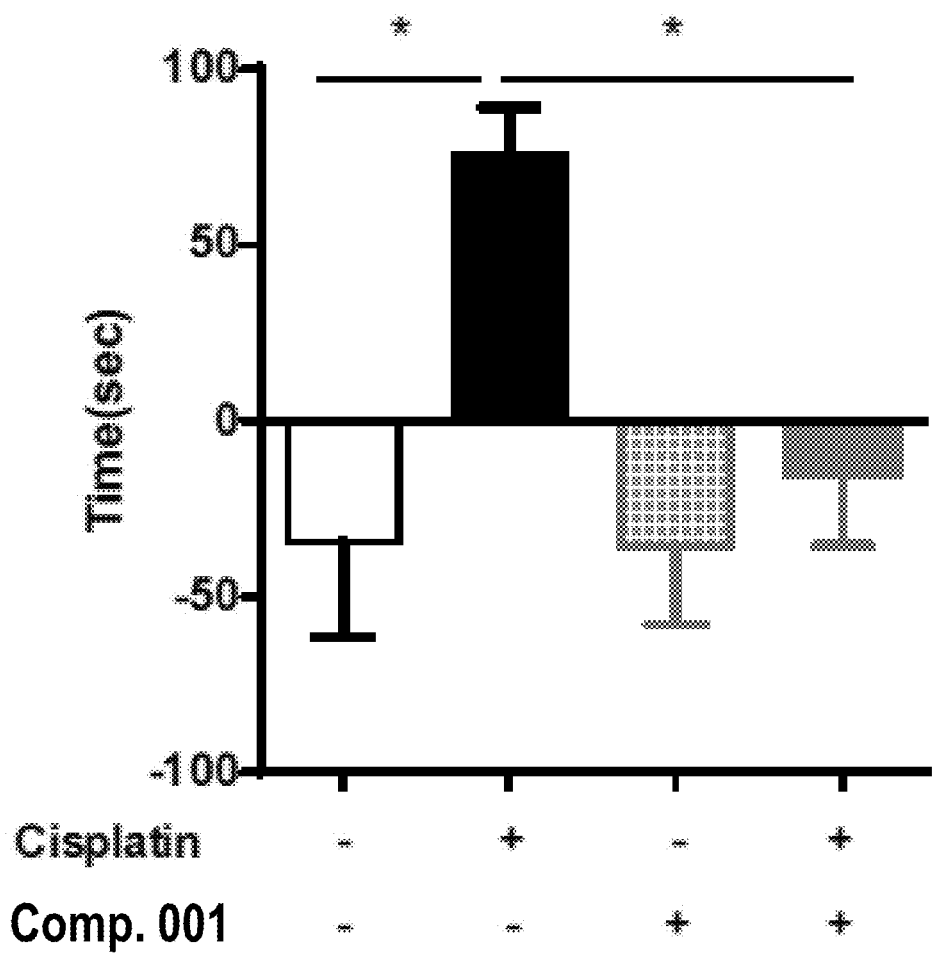

FIG. 8 shows spontaneous pain measured by the conditioned place preference test after two weeks of compound 001 treatment. Neuropathic pain was induced by two rounds of cisplatin treatment. During pre-conditioning, mice were allowed to freely explore for 15 min the CPP apparatus. The CPP apparatus consists of 2 chambers (18×20 cm, one dark, one white) connected by a 15 cm hallway (Stoelting, Wood Dale, Ill.). The time spent in the light chamber was recorded. During the conditioning phase, saline was injected i.p. in the morning and the mice were then kept in the dark chamber for 20 min. Three hours later, the analgesic retigabine (#R-100, Alomone laboratory, Jerusalem, Israel) was injected i.p. and the mice were immediately placed in the light chamber for 20 min. Conditioning was repeated for four consecutive days. The following day the mice did not receive any injections but were allowed to freely explore both chambers of the apparatus for 15 min. A mouse experiencing pain relieve by retigabine should show an increase in time spent in the light chamber that was paired with retigabine as compared to the pre-conditioning phase. The Y-axis indicates the change in time spent in light chamber. Two-way ANOVA revealed an effect of a group effect ($p<0.01$), and treatment (compound 001 vs. vehicle) effect ($p<0.01$). Tukey post-hoc analysis was used to determine differences between groups at specified time points. *$p<0.05$ between Cisplatin+Vehicle vs. all three other groups. n=6-8 mice/group.

Figure 9:
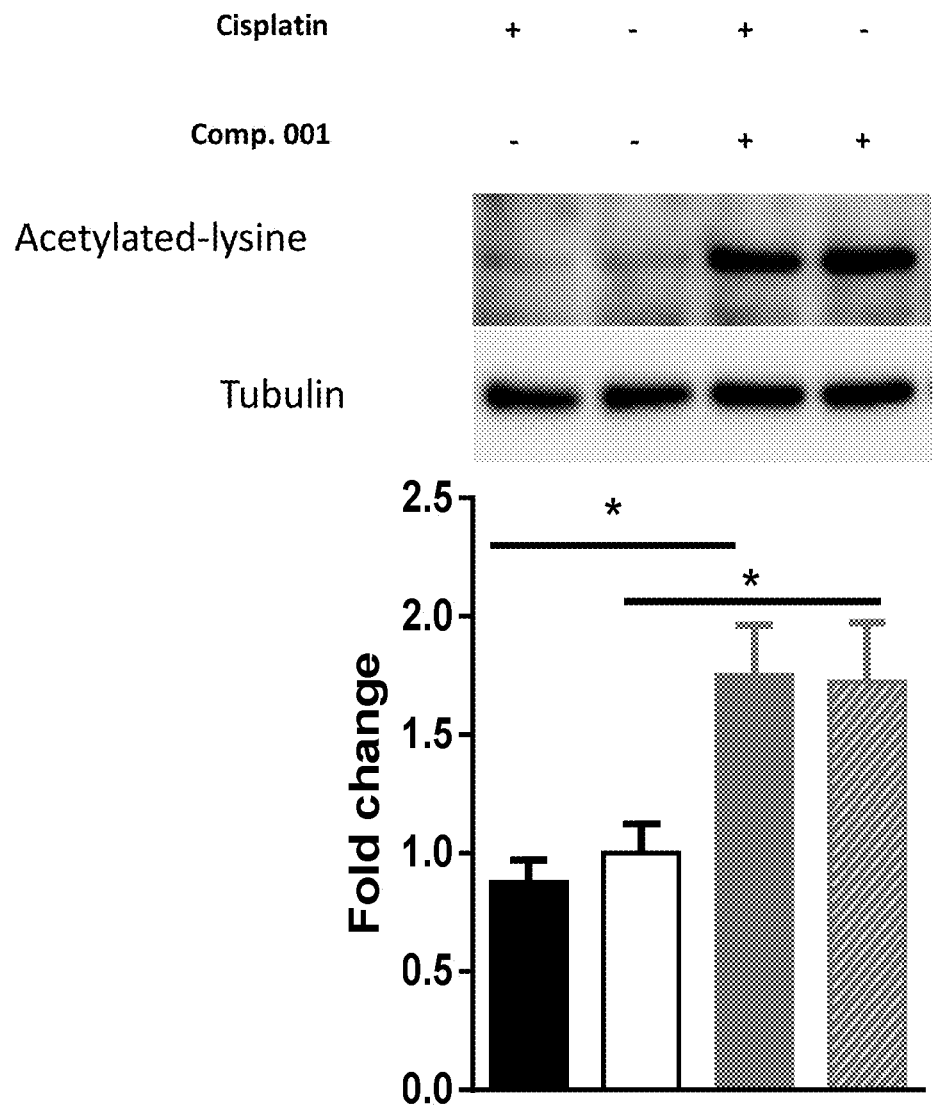

FIG. 9 shows acetylated α-tubulin levels in tibial nerves from mice that had received 2 cycles of cisplatin and 11 doses of compound 001 as assessed by Western blot analysis. Compound 001 treatment induced α-tubulin acetylation. n=4 mice/group. Two-way ANOVA revealed a significant treatment (compound 001) effect ($p<0.05$). Tukey post-hoc analysis revealed significant differences between groups: *$p<0.05$.

Figure 10:
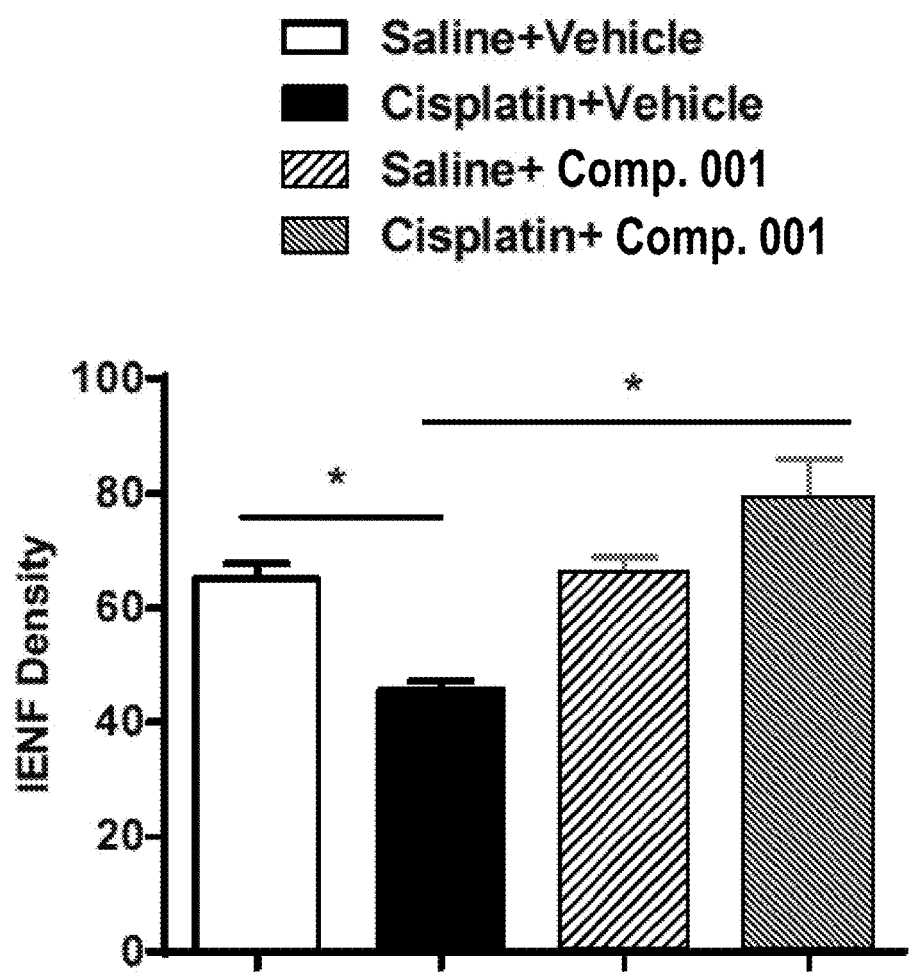

FIG. 10 shows quantification of intraepidermal nerve fiber (IENF) density expressed as the number of nerve fibers crossing the basement membrane/length of the basement membrane (mm) (n=4 mice per group), magnification X 40. Two-way ANOVA revealed a significant treatment (compound 001) effect ($p<0.05$). Tukey post-hoc analysis revealed significant differences between groups: *, $p<0.05$. Paw biopsies were obtained from the hind paws of mice that received 2 cycles of cisplatin and 11 doses of compound 001. Tissues were stained with antibodies for IENFs (PGP9.5) and collagen.

DETAILED DESCRIPTION

Chemotherapy-induced peripheral neuropathy (CIPN) is one of the most commonly and widely reported adverse side effects of cancer treatment (Dougherty P M, et al., Taxol-induced sensory disturbance is characterized by preferential impairment of myelinated fiber function in cancer patients. *Pain.* 2004; 109(1-2):132-42; Wolf S, et al. Chemotherapy-induced peripheral neuropathy: prevention and treatment strategies. *European journal of Cancer.* 2008; 44(11):1507-15). The overall incidence of CIPN ranges from 30-80% in patients treated for cancer depending on the chemotherapy regimens used and the duration of treatment, with the highest incidence reported for taxanes, platinum derivatives and vinca alkaloids (Wolf S, et al. *European journal of Cancer.* 2008; 44(11):1507-15; Cavaletti G, and Zanna C, Current status and future prospects for the treatment of chemotherapy-induced peripheral neurotoxicity. *European journal of cancer.* 2002; 38(14):1832-7; Cavaletti G, et al. Chemotherapy-induced neuropathy. *Curr Treat Options Neurol.* 2011; 13(2):180-90; Windebank A J and Grisold W, Chemotherapy-induced neuropathy. *Journal of the peripheral nervous system: JPNS.* 2008; 13(1):27-46; Seretny M, et al. Incidence, prevalence, and predictors of chemotherapy-induced peripheral neuropathy: A systematic review and meta-analysis. *Pain.* 2014; 155(12):2461-70; Park S B, et al. Chemotherapy-induced peripheral neurotoxicity: a critical analysis. *CA Cancer J Clin.* 2013; 63(6):419-37). The symptoms of CIPN include pain, numbness, tingling and temperature sensitivity, and normally present with a symmetric, distal, "stocking and glove" distribution (Dougherty P M, et al. *Pain.* 2004; 109(1-2):132-42; Wolf S, et al. *European journal of Cancer.* 2008; 44(11):1507-15; Cavaletti G, et al. The chemotherapy-induced peripheral neuropathy outcome measures standardization study: from consensus to the first validity and reliability findings. *Ann Oncol.* 2013; 24(2):454-62; Kim J H, et al. Basic science and clinical management of painful and non-painful chemotherapy-related neuropathy. *Gynecol Oncol.* 2015; 136(3):453-9). The occurrence of CIPN can limit the dosage, delay further treatment cycles, and in the worst scenarios lead to early termination of treatment (Pachman D R, et al. Chemotherapy-induced peripheral neuropathy: prevention and treatment. *Clin Pharmacol Ther.* 2011; 90(3):377-87; Cavaletti G, et al. Cisplatin-induced peripheral neurotoxicity is dependent on total-dose intensity and single-dose intensity. *Cancer.* 1992; 69(1):203-7; Uhm J H, and Yung W K. Neurologic Complications of Cancer Therapy. *Curr Treat Options Neurol.* 1999; 1(5):428-37; Polomano R C, and Bennett G J. Chemotherapy-evoked painful peripheral neuropathy. *Pain Med.* 2001; 2(1):8-14; Mielke S, Sparreboom A, and Mross K. Peripheral neuropathy: a persisting challenge in paclitaxel-based regimes. *European journal of cancer.* 2006; 42(1):24-30). Moreover, CIPN frequently persists for a prolonged period of time and sometimes even worsens after completion of chemotherapy (Quasthoff S, and Hartung H P. Chemotherapy-induced peripheral neuropathy. *J Neurol.* 2002; 249(1):9-17; Schneider B P, et al. Symptoms: Chemotherapy-Induced Peripheral Neuropathy. *Advances in experimental medicine and biology.* 2015; 862(77-87); Hershman D L, et al. Prevention and management of chemotherapy-induced peripheral neuropathy in survivors of adult cancers: American Society of Clinical Oncology clinical practice guideline. *Journal of clinical oncology.* 2014: 32(18):1941-67), thereby greatly reducing the quality of life for cancer survivors. Despite the high prevalence and severity of CIPN, currently there are no effective FDA-approved drugs to prevent or reverse CIPN.

Cisplatin is a platinum-based chemotherapeutic that is commonly used for the treatment of solid tumors such as lung, ovarian, testis, bladder, and head and neck cancer (Barabas K, et al. Cisplatin: a review of toxicities and therapeutic applications. *Veterinary and comparative oncology.* 2008; 6(1):1-18; Kelland L. The resurgence of platinum-based cancer chemotherapy. *Nat Rev Cancer.* 2007; 7(8):573-84). Cisplatin treatment is associated with a high incidence of CIPN (Cavaletti G, and Marmiroli P. Chemotherapy-induced peripheral neurotoxicity. *Nat Rev Neurol.* 2010; 6(12):657-66), and in rodents induces mechanical hyperalgesia, spontaneous pain and numbness (Authier N, et al. An animal model of nociceptive peripheral neuropathy following repeated cisplatin injections. *Exp Neurol.* 2003; 182(1):12-20; Qi-Liang Mao-Ying A K, et al. The antidiabetic drug metformin protects against chemotherapy-induced peripheral neuropathy in a mouse model. *Clinical Cancer Research.* 2014; Krukowski K, et al. Prevention of chemotherapy-induced peripheral neuropathy by the small-molecule inhibitor pifithrin-mu. *Pain.* 2015; 156(11):2184-92; Park H J, et al. Persistent hyperalgesia in the cisplatin-treated mouse as defined by threshold measures, the conditioned place preference paradigm, and changes in dorsal root ganglia activated transcription factor 3: the effects of gabapentin, ketorolac, and etanercept. *Anesth*

*Analg.* 2013; 116(1):224-31). Mechanisms that underlie development and maintenance of cisplatin-induced peripheral neuropathy are under active investigation. Chemotherapy-induced mitochondrial damage in peripheral sensory neurons is thought to play a major role in CIPN. Paclitaxel and oxaliplatin have been shown to cause mitochondrial swelling or vacuolization in cell bodies and axons of sensory neurons (Krukowski K, et al. Prevention of chemotherapy-induced peripheral neuropathy by the small-molecule inhibitor pifithrin-mu. *Pain.* 2015; 156(11):2184-92, 25-30; Flatters S J, and Bennett G J. Studies of peripheral sensory nerves in paclitaxel-induced painful peripheral neuropathy: evidence for mitochondrial dysfunction. *Pain.* 2006; 122(3):245-57; Zheng H, et al. Functional deficits in peripheral nerve mitochondria in rats with paclitaxel- and oxaliplatin-evoked painful peripheral neuropathy. *Exp Neurol.* 2011; 232(2):154-61; Xiao W H, et al. Mitochondrial abnormality in sensory, but not motor, axons in paclitaxel-evoked painful peripheral neuropathy in the rat. *Neuroscience.* 2011; 199(461-9); Janes K, et al. Bioenergetic deficits in peripheral nerve sensory axons during chemotherapy-induced neuropathic pain resulting from peroxynitrite-mediated post-translational nitration of mitochondrial superoxide dismutase. *Pain.* 2013; 154(11):2432-40; Abbott B, et al. Limits on gravitational-wave emission from selected pulsars using LIGO data. *Phys Rev Lett.* 2005; 94(18):181103; Bennett G J, et al. Mitotoxicity in distal symmetrical sensory peripheral neuropathies. *Nat Rev Neurol.* 2014; 10(6):326-36). In the peripheral nerves of paclitaxel and oxaliplatin-treated rats these mitochondrial morphological changes are associated with impaired Complex I-mediated and Complex II-mediated respiration and ATP production (Zheng H, et al. Functional deficits in peripheral nerve mitochondria in rats with paclitaxel- and oxaliplatin-evoked painful peripheral neuropathy. *Exp Neurol.* 2011; 232(2):154-61). It has recently been shown that prevention of paclitaxel-induced mitochondrial morphological abnormalities by the compound pifithrin-μ also prevented mechanical hyperalgesia induced by paclitaxel (Krukowski K, et al. Prevention of chemotherapy-induced peripheral neuropathy by the small-molecule inhibitor pifithrin-mu. *Pain.* 2015; 156(11):2184-92.). These findings further support the role of mitochondrial damage in the pathogenesis of CIPN.

Histone deacetylase 6 (HDAC6) is a cytoplasmic class II histone deacetylase (HDAC) that, in contrast to the other HDACs, has a specificity for non-histone proteins, including α-tubulin and HSP90. HDAC6-activity regulates multiple intracellular processes such as protein degradation, cell motility, and cell-cell interaction (31-33 Valenzuela-Fernandez A, et al. HDAC6: a key regulator of cytoskeleton, cell migration and cell-cell interactions. *Trends in cell biology.* 2008; 18(6):291-7; Hubbert C, et al. HDAC6 is a microtubule-associated deacetylase. *Nature.* 2002; 417(6887):455-8; Zhang Y, Li N, Caron C, Matthias G, Hess D, Khochbin S, and Matthias P. HDAC-6 interacts with and deacetylates tubulin and microtubules in vivo. *EMBO J.* 2003; 22(5): 1168-79). Importantly, HDAC6 has been implicated in the regulation of mitochondrial transport (Hubbert C, et al. HDAC6 is a microtubule-associated deacetylase. *Nature.* 2002; 417(6887):455-8; Zhang Y, et al. HDAC-6 interacts with and deacetylates tubulin and microtubules in vivo. *EMBO J.* 2003; 22(5):1168-79; Reed N A, et al. Microtubule acetylation promotes kinesin-1 binding and transport. *Curr Biol.* 2006; 16(21):2166-72). In vitro, HDAC6 inhibition increased α-tubulin acetylation and promoted mitochondrial transport in hippocampal neurons (Chen S, et al. HDAC6 regulates mitochondrial transport in hippocampal neurons. *PLoS One.* 2010; 5(5):e10848). In vivo, it has been shown that an HDAC6 inhibitor increased α-tubulin acetylation in peripheral nerves and improved sensory-motor function in a mouse model of type 2 Charcot-Marie-Tooth (CMT2) disease. In this model, the HDAC6 inhibitor also enhanced mitochondrial transport as measured in DRG explants (d'Ydewalle C, et al. HDAC6 inhibitors reverse axonal loss in a mouse model of mutant HSPB 1-induced Charcot-Marie-Tooth disease. *Nature Medicine.* 2011; 17(8):968-74).

Definitions

Listed below are definitions of various terms used in this disclosure. These definitions apply to the terms as they are used throughout this specification and claims, unless otherwise limited in specific instances, either individually or as part of a larger group.

The term "about" generally indicates a possible variation of no more than 10%, 5%, or 1% of a value. For example, "about 25 mg/kg" will generally indicate, in its broadest sense, a value of 22.5-27.5 mg/kg, i.e., 25±2.5 mg/kg.

The term "HDAC" refers to histone deacetylases, which are enzymes that remove the acetyl groups from the lysine residues in core histones, thus leading to the formation of a condensed and transcriptionally silenced chromatin. There are currently 18 known histone deacetylases, which are classified into four groups. Class I HDACs, which include HDAC1, HDAC2, HDAC3, and HDAC8, are related to the yeast RPD3 gene. Class II HDACs, which include HDAC4, HDAC5, HDAC6, HDAC7, HDAC9, and HDAC10, are related to the yeast Hda1 gene. Class III HDACs, which are also known as the sirtuins are related to the Sir2 gene and include SIRT1-7. Class IV HDACs, which contains only HDAC11, has features of both Class I and II HDACs. The term "HDAC" refers to any one or more of the 18 known histone deacetylases, unless otherwise specified.

The term "inhibitor" is synonymous with the term antagonist.

The term "selective inhibitor" means an inhibitor that substantially inhibits (5 to 1000-fold or more) the activity of a specific molecule. For example, a selective inhibitor of HDAC6 (also referred to herein as a histone deacetylase 6 selective inhibitor) substantially inhibits the activity of HDAC6 as compared with other HDACs (i.e., inhibits the activity of HDAC6 to a much greater extent, e.g., 5 to 1000-fold or more, than other HDACs).

The term "pharmaceutically acceptable salt" refers to those salts of the compounds formed by the process disclosed herein which are, within the scope of sound medical judgment, suitable for use in contact with the tissues of humans and lower animals without undue toxicity, irritation, allergic response and the like, and are commensurate with a reasonable benefit/risk ratio. Additionally, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non-toxic salts of the parent compound formed, for example, from non-toxic inorganic or organic acids. Pharmaceutically acceptable salts can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

The term "subject" refers to a mammal. A subject therefore refers to, for example, dogs, cats, horses, cows, pigs, guinea pigs, and the like. Preferably the subject is a human. When the subject is a human, the subject can also be referred to herein as a patient.

The terms "treating," "treatment" and the like are used herein to mean obtaining a desired pharmacologic and/or physiologic effect that at least alleviates or abates a disease and/or its attendant symptoms. "Treating" also covers any treatment of a disease in a mammal, and includes inhibiting a disease, i.e., arresting its development; or relieving or ameliorating the disease, e.g., cause regression of the disease. As used herein, to "treat" includes systemic amelioration of the symptoms associated with the pathology and/or a delay in onset of symptoms. Clinical and sub-clinical evidence of "treatment" will vary with the pathology, the individual and the treatment. The terms "prevent," "preventing," or "prevention" as used herein comprises the prevention of at least one symptom associated with or caused by the state, disease or disorder being prevented.

The number of carbon atoms in an alkyl substituent can be indicated by the prefix "$C_{x-y}$," where x is the minimum and y is the maximum number of carbon atoms in the substituent. Likewise, a $C_x$ chain means an alkyl chain containing x carbon atoms.

The term "alkyl" refers to saturated, straight- or branched-chain hydrocarbon moieties containing, in certain embodiments, between one and six, or one and eight carbon atoms, respectively. Examples of $C_{1-6}$-alkyl moieties include, but are not limited to, methyl, ethyl, propyl, isopropyl, n-butyl, tert-butyl, neopentyl, n-hexyl moieties; and examples of $C_{1-8}$-alkyl moieties include, but are not limited to, methyl, ethyl, propyl, isopropyl, n-butyl, tert-butyl, neopentyl, n-hexyl, heptyl, and octyl moieties.

The term "alkoxy" refers to an —O-alkyl moiety.

The terms "halo" and "halogen" refer to an atom selected from fluorine, chlorine, bromine and iodine. The term "haloalkyl" refers to an alkyl group with one more instances of halo substitution, e.g., —CF₃.

The term "cycloalkyl" denotes a monovalent group derived from a monocyclic or polycyclic saturated or partially unsaturated carbocyclic ring compound. Examples of $C_{3-8}$-cycloalkyl include, but are not limited to, cyclopropyl, cyclobutyl, cyclopentyl, cyclohexyl, cycloheptyl and cyclooctyl; and examples of $C_{3-12}$-cycloalkyl include, but are not limited to, cyclopropyl, cyclobutyl, cyclopentyl, cyclohexyl, bicyclo [2.2.1] heptyl, and bicyclo [2.2.2] octyl. Also contemplated are monovalent groups derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heterocycloalkyl" refers to a non-aromatic 3-, 4-, 5-, 6- or 7-membered ring or a bi- or tri-cyclic group fused of non-fused system, where (i) each ring contains between one and three heteroatoms independently selected from oxygen, sulfur, and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

Any of the aryls, substituted aryls, heteroaryls and substituted heteroaryls described herein, can be any aromatic group.

Combinations of substituents and variables disclosed herein are only those that result in the formation of stable compounds. The term "stable" refers to compounds which possess stability sufficient to allow manufacture and which maintains the integrity of the compound for a sufficient period of time to be useful for the purposes detailed herein (e.g., therapeutic or prophylactic administration to a subject).

Selective Inhibitors of HDAC6

Small molecules that specifically inhibit HDAC6 and can alleviate pain and numbness associated with administration of cisplatin are disclosed herein. In one embodiment, the HDAC6 selective inhibitor is a compound of Formula (I):

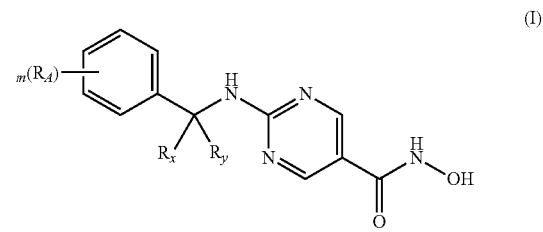

(I)

or a pharmaceutically acceptable salt thereof, wherein, $R_x$ and $R_y$ together with the carbon to which each is attached, form a cyclopropyl, cyclobutyl, cyclopentyl, cyclohexyl, cycloheptyl, cyclooctyl, or terahydropyranyl, any of which may be optionally substituted with 1 or 2 $R_Z$;

$R_Z$ is independently, at each occurrence, selected from the group consisting of $C_{1-6}$-alkyl, $C_{1-6}$-alkoxy, halo, —$C_{1-6}$ haloalkyl, —$C_{1-6}$ dihaloalkyl, —$C_{1-6}$ trihaloalkyl, —OH, —N(R¹)₂, —C(O)R¹, —CO₂R¹, and —C(O)N(R¹)₂;

or:

two $R_Z$ groups on the same or adjacent carbon atoms are taken together to form a $C_{3-8}$-cycloalkyl or $C_{3-7}$-heterocycloalkyl ring, each of which may be fused or isolated;

each $R_A$ is independently $C_{1-6}$-alkyl, $C_{1-6}$-alkoxy, halo, OH or haloalkyl;

each R¹ is independently, at each occurrence, selected from the group consisting of H, $C_{1-6}$-alkyl, $C_{3-8}$-cycloalkyl, $C_{3-7}$-heterocycloalkyl, aryl, heteroaryl, $C_{1-6}$-alkyl-cycloalkyl, $C_{1-6}$-alkyl-heterocycloalkyl, $C_{1-6}$-alkyl-aryl, and $C_{1-6}$-alkyl-heteroaryl; and m is 0, 1, or 2.

In an embodiment, $R_Z$ is independently, at each occurrence, selected from the group consisting of $C_{1-6}$-alkyl, $C_{1-6}$-alkoxy, halo, —$C_{1-6}$ haloalkyl, —$C_{1-6}$ dihaloalkyl, —$C_{1-6}$ trihaloalkyl, —OH, —N(R¹)₂, —C(O)R¹, —CO₂R¹, and —C(O)N(R¹)₂. In a further embodiment, $R_Z$ is independently, at each occurrence, selected from the group consisting of $C_{1-6}$-alkyl, $C_{1-6}$-alkoxy, halo, —$C_{1-6}$ haloalkyl, —$C_{1-6}$ dihaloalkyl, —$C_{1-6}$ trihaloalkyl, and —OH In an embodiment, $R_x$ and $R_y$ together with the carbon to which each is attached, form a cyclopropyl, cyclobutyl, cyclopentyl, cyclohexyl, cycloheptyl, cyclooctyl, or terahydropyranyl, wherein the cyclopropyl, cyclobutyl, cyclopentyl, cyclohexyl, cycloheptyl, cyclooctyl, or terahydropyranyl is substituted with 1 or 2 $R_z$.

In an embodiment, $R_x$ and $R_y$ together with the carbon to which each is attached, form a cyclohexyl, wherein the cyclohexyl is substituted with 1 or 2 halo.

In another embodiment, the HDAC6 selective inhibitor is a compound 001:

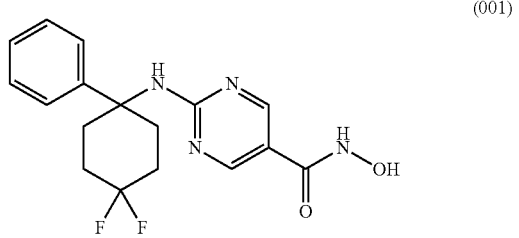 [SMILES: O=C(NO)c1cnc(NC2(c3ccccc3)CCC(F)(F)CC2)nc1]

(001)

or a pharmaceutically acceptable salt thereof.

In some embodiments, the compound has a selectivity for HDAC6 that is 5 to 1000 fold greater than for other HDACs. In other embodiments, the compound has a selectivity for HDAC6 when tested in a HDAC enzyme assay, of about 5 to 1000 fold greater than for other HDACs. This is seen in Table 1, which shows the $IC_{50}$ values for compound 001 on four different HDACs. These $IC_{50}$ values and the HDAC assay used to obtain said values are disclosed in U.S. patent application Ser. No. 14/631,971, now published as U.S. Publication No. 2015/0239869, which is hereby incorporated by reference in its entirety.

an otherwise recalcitrant cancer (Warrell et al. *J. Natl. Cancer Inst.*, 1998, 90, 1621-1625). Eleven human HDACs, which use Zn as a cofactor, have been identified (Taunton et al. *Science* 1996, 272, 408-411; Yang et al. *J. Biol. Chem.* 1997, 272, 28001-28007; Grozinger et al. *Proc. Natl. Acad. Sci. U.S.A.* 1999, 96, 4868-4873; Kao et al. *Genes Dev.* 2000, 14, 55-66; Hu et al. *J. Biol. Chem.* 2000, 275, 15254-15264; Zhou et al. *Proc. Natl. Acad. Sci.*, 2001, 98, 10572-10577; Venter et al. *Science*, 2001, 291, 1304-1351), and these members fall into three classes (class I, II, and IV). An additional seven HDACs have been identified which use NAD as a cofactor.

Histone deacetylases are known to play an essential role in the transcriptional machinery for regulating gene expression, induce histone hyperacetylation and to affect the gene expression. Therefore, it is useful as a therapeutic or prophylactic agent for diseases caused by abnormal gene expression such as, for example, inflammatory disorders, diabetes, diabetic complications, homozygous thalassemia, fibrosis, cirrhosis, acute promyelocytic leukemia (APL), organ transplant rejections, autoimmune diseases, protozoal infections, tumors, etc. HDAC inhibition is a promising therapeutic approach for the treatment of a range of central nervous system disorders (Langley B, et al., 2005, Current Drug Targets, *CNS & Neurological Disorders*, 4: 41-50).

Herein, it is demonstrated that pharmacological inhibition of HDAC6 with Compound 001 effectively prevents and reverses cisplatin-induced mechanical hyperalgesia; moreover, it was shown that prolonged treatment of compound 001 also reverses cisplatin-induced spontaneous pain and numbness. Compound 001 has been identified as a single agent capable of causing full recovery from multiple symptoms of CIPN. The reversal of cisplatin-induced neuropathy by inhibition of HDAC6 was associated with normalization of cisplatin-induced mitochondrial bioenergetic deficits and

TABLE 1

$IC_{50}$ values (nM) for compound 001 on four different HDACs

| Structure | HDAC1 | HDAC2 | HDAC3 | HDAC6 |
|---|---|---|---|---|
| 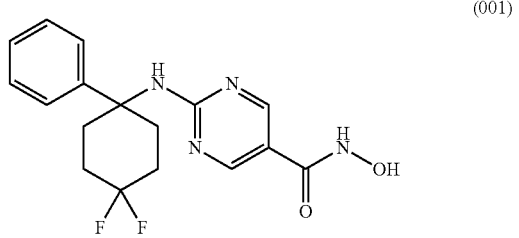 [SMILES: O=C(NO)c1cnc(NC2(c3ccccc3)CCC(F)(F)CC2)nc1] | 961 | 982 | 4380 | 3.7 |

Methods

One biological target of recent interest is histone deacetylase (HDAC) (see, for example, a discussion of the use of inhibitors of histone deacetylases for the treatment of cancer: Marks et al. *Nature Reviews Cancer*, 2001, 7,194; Johnstone et al. *Nature Reviews Drug Discovery*, 2002, 287). Post-translational modification of proteins through acetylation and deacetylation of lysine residues plays a critical role in regulating their cellular functions. HDACs are zinc hydrolases that modulate gene expression through deacetylation of the N-acetyl-lysine residues of histone proteins and other transcriptional regulators (Hassig et al. *Curr. Opin. Chem. Biol.* 1997, 1, 300-308). HDACs participate in cellular pathways that control cell shape and differentiation, and an HDAC inhibitor has been shown effective in treating mitochondrial content in the distal axons in the tibial nerve. Normalization of mitochondrial bioenergetics occurred together with restoration of IENF density. These results identify HDAC6 as a novel therapeutic target for treatment of existing cisplatin-induced peripheral neuropathy. The ability of compound 001 to reverse existing symptoms of CIPN is an important finding as there are no FDA-approved therapeutics for treatment of established CIPN.

Bioenergetic deficits associated with neuronal mitochondrial dysfunction have been proposed as a driver for CIPN (Bennett G J, et al. Mitotoxicity in distal symmetrical sensory peripheral neuropathies. *Nat. Rev. Neurol.* 2014; 10(6):326-36). The symptoms of CIPN present in a distal to proximal "stocking and glove" distribution, with the longest peripheral axons having the highest susceptibility. This pattern of symptoms suggests that insufficient distribution of mitochondria to the peripheral axons might well contribute to CIPN. Indeed, the results implicate impaired mitochondrial transport as a contributing factor to cisplatin-induced peripheral neuropathy. In the ex vivo model of DRG neuron cultures, cisplatin-treatment reduced mitochondrial movement in the axons, which was reversed by the HDAC6 inhibitor compound 001 (FIG. 6). The mitochondrial transport in vivo was not directly measured. However, it was shown that compound 001 improved mitochondrial bioenergetics and mitochondrial content in the distal tibial nerves of cisplatin treated mice (FIGS. 7A-C). These findings provide indirect evidence implicating improved axonal mitochondrial transport in the beneficial effects of HDAC6 inhibition. Others have also proposed that inhibition of HDAC6 protects against neurological disorders by facilitating distribution of mitochondria throughout the neuronal network (d'Ydewalle C, et al. HDAC6 inhibitors reverse axonal loss in a mouse model of mutant HSPB 1-induced Charcot-Marie-Tooth disease. *Nature Medicine.* 2011; 17(8):968-74; Dompierre J P, et al. Histone deacetylase 6 inhibition compensates for the transport deficit in Huntington's disease by increasing tubulin acetylation. *The Journal of Neuroscience.* 2007; 27(13):3571-83; Godena V K, et al. Increasing microtubule acetylation rescues axonal transport and locomotor deficits caused by LRRK2 Roc-COR domain mutations. *Nature Communications.* 2014; 5(5245); Reynolds I J, et al. Mitochondrial trafficking in neurons: a key variable in neurodegeneration? *J Bioenerg Biomembr.* 2004; 36(4):283-6; Beal M F. Mitochondria and neurodegeneration. *Novartis Found Symp.* 2007; 287(183-92; discussion 92-6). The transport of mitochondria along microtubules is increased by acetylation of α-tubulin, which provides a recognition signal for the anchoring of molecular motors (Reed N A, et al. Microtubule acetylation promotes kinesin-1 binding and transport. *Curr Biol.* 2006; 16(21):2166-72). HDAC6 is a well-known α-tubulin deacetylase and inhibition of HDAC6 increases tubulin acetylation. Indeed, increased acetylation of α-tubulin by HDAC6 inhibition is associated with improved mitochondrial transport (Hubbert C, et al. HDAC6 is a microtubule-associated deacetylase. *Nature.* 2002; 417(6887):455-8; Chen S, et al. HDAC6 regulates mitochondrial transport in hippocampal neurons. *PLoS One.* 2010; 5(5):e10848; d'Ydewalle C, et al. HDAC6 inhibitors reverse axonal loss in a mouse model of mutant HSPB 1-induced Charcot-Marie-Tooth disease. *Nature Medicine.* 2011; 17(8):968-74). In the model of cisplatin-induced peripheral neuropathy, it was shown that inhibition of HDAC6 with compound 001 promoted α-tubulin acetylation (FIG. 9). Corresponding with increased α-tubulin acetylation, it was shown that compound 001 improved mitochondrial bioenergetics and contents in the distal tibial nerves of cisplatin-treated mice. Taken together, these data support a protective role for HDAC6 inhibition in CIPN through increasing α-tubulin acetylation and improving axonal mitochondrial transport.

IENF loss has been suggested as the earliest sign of axonal pathology. It is hypothesized that the IENFs represent bioenergetically active regions and therefore are highly susceptible to chemotherapy-induced mitotoxic insults (Bennett G J, et al. Mitotoxicity in distal symmetrical sensory peripheral neuropathies. *Nat Rev Neurol.* 2014; 10(6):326-36). Consistent with previous reports (Qi-Liang Mao-Ying A K, Karen Krukowski, Xiao-Jiao Huo, Theodore J. Price, Charles Cleeland, and Cobi J. Heijnen. The anti-diabetic drug metformin protects against chemotherapy-induced peripheral neuropathy in a mouse model. *Clinical Cancer Research.* 2014; Lauria G, Lombardi R, Borgna M, Penza P, Bianchi R, Savino C, Canta A, Nicolini G, Marmiroli P, and Cavaletti G. Intraepidermal nerve fiber density in rat foot pad: neuropathologic-neurophysiologic correlation. *Journal of the peripheral nervous system: JPNS.* 2005; 10(2):202-8), it was shown that cisplatin-treatment decreased IENF density in the hind paws. Importantly, two weeks of compound 001 treatment fully reversed cisplatin-induced IENF loss (FIG. 10) and restored distal nerve mitochondrial bioenergetics (FIGS. 7A-C). As nerve fiber regrowth and extension is a highly energetically demanding process (Bennett G J, et al. Terminal arbor degeneration—a novel lesion produced by the antineoplastic agent paclitaxel. *The European journal of neuroscience.* 2011; 33(9):1667-76), the effect of compound 001 on IENF is likely attributable to the normalization of mitochondrial bioenergetics in the peripheral axons. Therefore, these data provide important evidence for the mitotoxic hypothesis of IENF loss in CIPN. Importantly, it was shown that prolonged inhibition of HDAC6 with compound 001 reversed IENF loss and at the same time led to persistent recovery from multiple symptoms of CIPN. Clinically IENF loss has been regarded as a reliable diagnostic tool for peripheral neuropathy (Lauria G, and Lombardi R. Skin biopsy: a new tool for diagnosing peripheral neuropathy. *Bmj.* 2007; 334(7604):1159-62) and these data indicate that restoration of IENF density may be used as a biomarker to evaluate drug efficacy and predict long-term recovery in CIPN patients.

These findings strongly implicate changes in α-tubulin acetylation and improved mitochondrial transport in the reversal of CIPN by HDAC6 inhibition. However, it is possible that compound 001 also impacts other cellular processes. For example, HDAC6 inhibition has been implicated in redox regulation by increasing acetylation of peroxiredoxins-1 and -2, thereby increasing their reducing activity (Parmigiani R B, et al. HDAC6 is a specific deacetylase of peroxiredoxins and is involved in redox regulation. *Proceedings of the National Academy of Sciences.* 2008; 105(28):9633-8). An anti-inflammatory effect of selective HDAC6 inhibition has also been implicated in its beneficial effects in models of rheumatoid arthritis (Vishwakarma S, et al. Tubastatin, a selective histone deacetylase 6 inhibitor shows anti-inflammatory and anti-rheumatic effects. *International Immunopharmacology.* 2013; 16(1):72-8). In addition, there is evidence that HDAC6 inhibition amplifies the production of the anti-inflammatory cytokine interleukin-10 that is known to have pain-reducing effects (Wang B, Rao Y H, Inoue M, Hao R, Lai C H, Chen D, McDonald S L, Choi M C, Wang Q, Shinohara M L, et al. Microtubule acetylation amplifies p38 kinase signalling and anti-inflammatory IL-10 production. *Nature Communications.* 2014; 5(3479); Milligan E D, Penzkover K R, Soderquist R G, and Mahoney M J. Spinal interleukin-10 therapy to treat peripheral neuropathic pain. *Neuromodulation.* 2012; 15(6):520-6). Compound 001 treatment reversed cisplatin-induced astrocyte activation, implicating a potential contribution of anti-inflammatory effects to the efficacy of compound 001. As both oxidative stress and inflammatory cascade activation have been implicated in the initiation and progression of CIPN (Areti A, et al. Oxidative stress and nerve damage: role in chemotherapy induced peripheral neuropathy. *Redox Biology.* 2014; 2(289-95); Wang X M, et al. Discovering cytokines as targets for chemotherapy-induced painful peripheral neuropathy. *Cytokine.* 2012; 59(1):3-9), inhibition of HDAC6 might also promote resolution of CIPN through targeting these pathways. Further studies will be needed to determine the involvement of other pathways in the protective effects of HDAC6 inhibition against CIPN.

When investigating potential therapeutics for CIPN, it is critical that such treatments do not interfere with the antitumor effects of chemotherapy. The HDAC6 inhibitor ricolinostat has been shown to have synergistic effect with proteasome inhibitors for the treatment of multiple myeloma in both preclinical and clinical settings (Santo L, et al. Preclinical activity, pharmacodynamic, and pharmacokinetic properties of a selective HDAC6 inhibitor, ACY-1215, in combination with bortezomib in multiple myeloma. *Blood.* 2012; 119(11):2579-89; Mishima Y, et al. Ricolinostat induced inhibition of aggresome formation accelerates carfilzomib-induced multiple myeloma cell death. *British Journal of Haematology.* 2015; 169(3):423-34). The antitumor effects of HDAC6 inhibition are thought to be mediated by increases in acetylation of HSP90, which disrupts the chaperone function of HSP90, leading to misfolded protein aggregation in cancer cells and subsequent cancer cell death (Bali P, et al. Inhibition of histone deacetylase 6 acetylates and disrupts the chaperone function of heat shock protein 90: a novel basis for antileukemia activity of histone deacetylase inhibitors. *The Journal of Biological Chemistry.* 2005; 280(29):26729-34; Kovacs J J, et al. HDAC6 regulates Hsp90 acetylation and chaperone-dependent activation of glucocorticoid receptor. *Molecular Cell.* 2005; 18(5):601-7.). These studies in combination with the present findings indicate that HDAC6 inhibition could enhance tumor-killing effects of chemotherapeutics and at the same time inhibit CIPN.

CIPN represents an important challenge in cancer treatment due to the severity of symptoms and the lack of effective therapeutics for both prevention or treatment. It was shown that HDAC6 inhibition completely reversed multiple symptoms of CIPN. The protective effect of HDAC6 inhibition is associated with improved axonal mitochondrial bioenergetics, increased α-tubulin acetylation and enhanced IENF density. These findings provide important evidence for using HDAC6 inhibitors as promising therapeutics for prevention and treatment of CIPN. These results also implicate IENF density as a reliable biomarker for clinical evaluation of drug efficacy in the treatment of CIPN.

Thus, in an aspect, provided herein are methods of treating or preventing a cisplatin-induced peripheral neuropathy in a subject in need thereof comprising administering to the subject a therapeutically effective amount of a histone deacetylase 6 selective inhibitor.

In another aspect, provided herein are methods of treating or preventing a cisplatin-induced peripheral neuropathy in a subject in need thereof comprising administering to the subject a therapeutically effective amount of a compound of Formula (I), or a pharmaceutically acceptable salt thereof.

In an aspect, provided herein is a method of treating cisplatin-induced pain in a subject in need thereof comprising administering to the subject a therapeutically effective amount of a compound of Formula (I), or a pharmaceutically acceptable salt thereof.

In another aspect, provided herein is a method of treating cisplatin-induced numbness in a subject in need thereof comprising administering to the subject a therapeutically effective amount of a compound of Formula (I), or a pharmaceutically acceptable salt thereof.

In another aspect, provided herein is a method of preventing cisplatin-induced astrocyte activation in a subject in need thereof comprising administering to the subject a therapeutically effective amount of a compound of Formula (I), or a pharmaceutically acceptable salt thereof.

In another aspect, provided herein is a method of preventing cisplatin-induced decrease in neuronal mitochondrial transport in a neuron comprising contacting the neuron with an effective amount of a compound of Formula (I), or a pharmaceutically acceptable salt thereof.

In another aspect, provided herein is a method for restoring the loss of intra-epidermal nerve fiber (IENF) in a subject, comprising administering to the subject an effective amount of a compound of Formula (I), or a pharmaceutically acceptable salt thereof. In an embodiment, the loss of intra-epidermal nerve fiber is the result of administering cisplatin to the subject. In another embodiment, the administration of the compound of Formula (I), or a pharmaceutically acceptable salt thereof, to the subject occurs during or after administering cisplatin.

Methods of making the compounds of Formula (I) can be found in PCT application publication WO/2012068109A2.

In another aspect, provided herein are methods of treating or preventing a cisplatin-induced peripheral neuropathy in a subject in need thereof comprising administering to the subject a therapeutically effective amount of a compound 001:

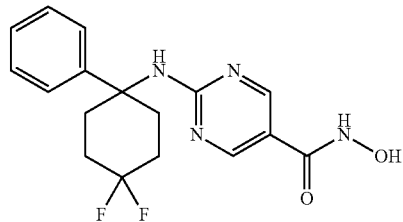 [SMILES: O=C(NO)c1cnc(NC2(c3ccccc3)CCC(F)(F)CC2)nc1]

or a pharmaceutical composition comprising compound 001, or a pharmaceutically acceptable salt thereof.

In an aspect, provided herein is a method of treating cisplatin-induced pain in a subject in need thereof comprising administering to the subject a therapeutically effective amount of compound 001, or a pharmaceutically acceptable salt thereof.

In another aspect, provided herein is a method of treating cisplatin-induced numbness in a subject in need thereof comprising administering to the subject a therapeutically effective amount of compound 001, or a pharmaceutically acceptable salt thereof.

In another aspect, provided herein is a method of preventing cisplatin-induced astrocyte activation in a subject in need thereof comprising administering to the subject a therapeutically effective amount of compound 001, or a pharmaceutically acceptable salt thereof.

In another aspect, provided herein is a method of preventing cisplatin-induced decrease in neuronal mitochondrial transport in a neuron comprising contacting the neuron with an effective amount of compound 001, or a pharmaceutically acceptable salt thereof.

In another aspect, provided herein is a method for restoring the loss of intra-epidermal nerve fiber (IENF) in a subject, comprising administering to the subject an effective amount of compound 001, or a pharmaceutically acceptable salt thereof. In an embodiment, the loss of intra-epidermal nerve fiber is the result of administering cisplatin to the subject. In another embodiment, the administration of compound 001, or a pharmaceutically acceptable salt thereof, to the subject occurs during or after administering cisplatin.

Methods of making compound 001 can be found in U.S. publication no. 2015/0239869.

In certain embodiments, provided herein is a method of treatment of any of the disorders described herein, wherein the subject is a human.

In another aspect, provided herein is a method of treating cancer in a subject in need thereof, comprising administering to the subject a therapeutically effective amount of cisplatin and a histone deacetylase 6 selective inhibitor.

In an embodiment, the histone deacetylase 6 selective inhibitor is a compound of Formula (I). In another embodiment, the histone deacetylase 6 selective inhibitor is compound 001.

In an embodiment, the cancer is selected from the group consisting of testicular cancer, ovarian cancer, bladder cancer, head and neck cancer, esophageal cancer, small and non-small cell lung cancer, breast cancer, cervical cancer, stomach cancer and prostate cancer. In another embodiment, the cancer is selected from the group consisting of Hodgkin's and non-Hodgkin's lymphomas, neuroblastoma, sarcomas, multiple myeloma, melanoma, and mesothelioma.

In another embodiment, the cancer is sarcoma, small cell lung cancer, ovarian cancer, lymphoma, bladder cancer, cervical cancer, or germ cell tumor.

In accordance with the foregoing, the present disclosure further provides a method for treating any of the diseases or disorders described above in a subject in need of such treatment, which method comprises administering to said subject a therapeutically effective amount of a compound disclosed herein or a pharmaceutically acceptable salt thereof. For any of the above uses, the required dosage will vary depending on the mode of administration, the particular condition to be treated and the effect desired.

According to the methods of treatment of the present disclosure, disorders are treated or prevented in a subject, such as a human or other animal, by administering to the subject a therapeutically effective amount of a compound disclosed herein, in such amounts and for such time as is necessary to achieve the desired result. The term "therapeutically effective amount" of a compound disclosed herein means a sufficient amount of the compound so as to decrease the symptoms of a disorder in a subject. As is well understood in the medical arts a therapeutically effective amount of a compound disclosed herein will be at a reasonable benefit/risk ratio applicable to any medical treatment.

In general, compounds provided herein will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight (0.05 to 4.5 mg/m$^2$). An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

In certain embodiments, a therapeutic amount or dose of the compounds disclosed herein may range from about 0.1 mg/kg to about 500 mg/kg (about 0.18 mg/m$^2$ to about 900 mg/m$^2$), alternatively from about 1 to about 50 mg/kg (about 1.8 to about 90 mg/m$^2$). In general, treatment regimens comprise administration to a patient in need of such treatment from about 10 mg to about 1000 mg of the compound(s) disclosed herein per day in single or multiple doses. Therapeutic amounts or doses will also vary depending on route of administration, as well as the possibility of co-usage with other agents.

Upon improvement of a subject's condition, a maintenance dose of a compound, composition or combination may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions disclosed herein will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Pharmaceutical Compositions

In another aspect, the provided herein is a pharmaceutical composition comprising a compound of Formula (I), or a pharmaceutically acceptable salt thereof, for use in treating or preventing a cisplatin-induced neuropathy.

In another aspect, disclosed herein is a pharmaceutical composition comprising compound 001, or a pharmaceutically acceptable salt thereof, together with a pharmaceutically acceptable carrier for use in treating or preventing a cisplatin-induced neuropathy.

The pharmaceutical compositions disclosed herein comprise a therapeutically effective amount of a compound disclosed herein formulated together with one or more pharmaceutically acceptable carriers. The term "pharmaceutically acceptable carrier" means a non-toxic, inert solid, semi-solid or liquid filler, diluent, encapsulating material or formulation auxiliary of any type. The pharmaceutical compositions disclosed herein can be administered to humans and other animals orally, rectally, parenterally, intracisternally, intravaginally, intraperitoneally, topically (as by powders, ointments, or drops), buccally, or as an oral or nasal spray.

Compounds disclosed herein can be administered as pharmaceutical compositions by any conventional route, in particular enterally, for example, orally, e.g., in the form of tablets or capsules, or parenterally, e.g., in the form of injectable solutions or suspensions, topically, e.g., in the form of lotions, gels, ointments or creams, or in a nasal or suppository form.

Pharmaceutical compositions comprising a compound disclosed herein in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound disclosed herein with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

EXAMPLES

Examples have been set forth below for the purpose of illustration and to describe certain specific embodiments of the invention. However, the scope of the claims is not to be in any way limited by the examples set forth herein. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Chemotherapy-induced peripheral neuropathy (CIPN) characterized by pain and numbness is one of the most commonly reported dose-limiting side-effects of cancer treatment. There is growing evidence for chemotherapy-induced mitochondrial damage in peripheral nerves as a cause of CIPN. Histone deacetylase 6 (HDAC6) is a microtubule-associated deacetylase that regulates α-tubulin-dependent intracellular transport of mitochondria. The specific HDAC6 inhibitor, compound 001, was examined for its capacity to treat cisplatin-induced peripheral neuropathy. Pharmacological inhibition of HDAC6 with compound 001 prevented cisplatin-induced mechanical hyperalgesia. More importantly, treatment with compound 001 after neuropathy had been established completely reversed cisplatin-induced mechanical hyperalgesia, spontaneous pain, and numbness. Mechanistically, compound 001 treatment increased α-tubulin acetylation in the peripheral nerve. Compound 001 also restored the impaired mitochondrial motility in cisplatin-treated primary cultures of DRG neurons. Moreover, in vivo treatment with compound 001 rescued the cisplatin-induced reduction in mitochondrial function and content in the distal tibial nerves. Treatment with compound 001 also restored the loss of intra-epidermal nerve fiber (IENF) density in cisplatin-treated mice. These results demonstrate that pharmacological inhibition of HDAC6 completely reverses established cisplatin-induced peripheral neuropathy. The beneficial effects of HDAC6 inhibition on sensory function are associated with normalization of mitochondrial content and mitochondrial bioenergetics in the distal nerve, and restoration of intra-epidermal innervation.

Example 1: Synthesis of Compound 001

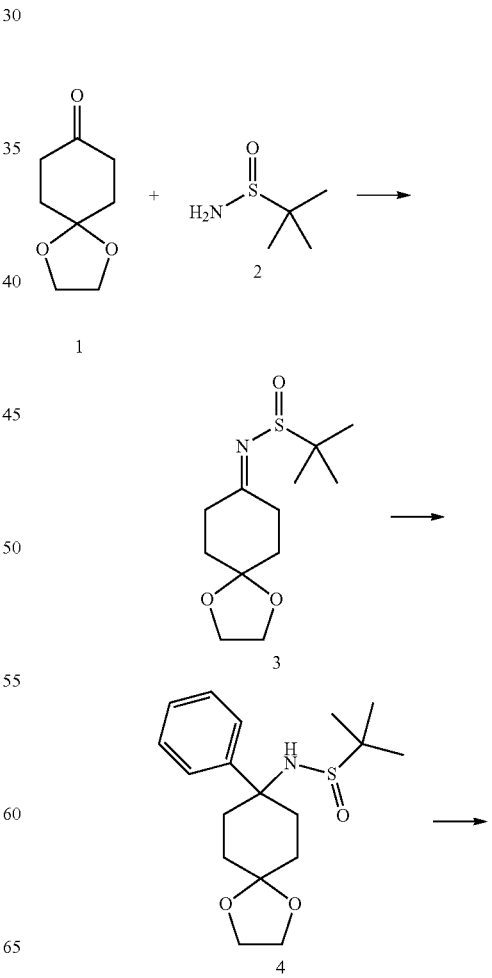

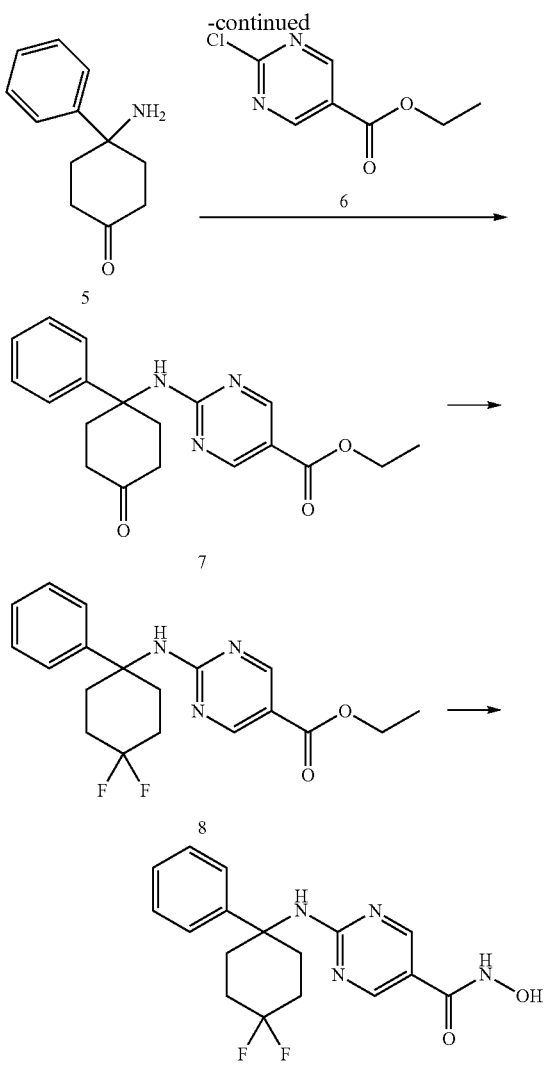

Methods of synthesizing compound 001 are also disclosed in U.S. patent application Ser. No. 14/631,971; filed Feb. 26, 2015; Mazitschek and van Duzer, inventors.

Step 1:

To a solution of 1 (2.00 g, 12.81 mmol) and 2 (1.552 g, 12.81 mmol) in THF (20 mL) was added Ti(OEt)$_4$ (5.4 mL, 25.56 mmol). The mixture was stirred at r.t. for 16 hrs and then poured into saturated NaHCO$_3$ solution at 0° C. The resulting precipitate was filtered off. The resulting filtrate was extracted with EA. The combined EA layers were concentrated in vacuo and the residue was purified by silica gel chromatography (PE/EA=4/1, 2/1) to afford 3 as a white solid (2.61 g, yield: 75%).

Step 2:

To a flask containing 3 (1.00 g, 3.86 mmol) was added a solution of PhMgBr (1 M in THF, 10 mL) at 0° C. It was stirred at 0° C. to rt until a complete reaction. Saturated NH$_4$Cl solution was added to adjust pH 6-7. The resulting mixture was extracted with EA. The combined EA layers were concentrated in vacuo and the residue was purified by silica gel chromatography (PE/EA=5/1, 2/1, 1.5/1) to afford 4 as a white solid (823 mg, yield: 60%).

Step 3:

A mixture of compound 4 (8.3 mg, 2.38 mmol) in HCl (2M in water, 20 mL) and THF (20 mL) was stirred at 50° C. for 16 hrs. A solution of NaOH was added to the mixture to adjust pH 7-8. THF was removed in vacuo and the aqueous phase was extracted with EA. The combined EA layers were concentrated in vacuo and the residue was dissolved in EA. HCl (4 M, 1 mL) was added. The resulting white solid was collected by filtration to afford desired product 5 (395 mg, yield: 57%).

Step 4:

A mixture of compound 5 (350 mg, 1.55 mmol), 6 (376 mg, 2.02 ml), and DIPEA (1.07 mt, 6.47 mmol) in NMP (4 mL) mixture was stirred at 130° C. for 5 hrs. The mixture was added water (20 mL), extracted with EA (25 mL×2). The organic layer was concentrated to get a residue, which was purified by silica gel chromatography (PE/EA=4/1) to afford 7 (178 mg, yield: 34%).

Step 5:

To a solution of compound 7 (168 mg, 0.50 mmol) in DCM (30 mL) was added DAST (302 μL, 2.47 mmol) at 0° C. It was stirred at rt for 3 hrs and 35° C. for 2 hrs. The reaction mixture was quenched with saturated NaHCO$_3$ (5 mL), and extracted with EtOAc (2×5 mL). The organic extracts were concentrated in vacuo. The residue was purified by pre-TLC to give 8 (74 mg, yield: 42%).

Step 6:

NH$_2$OH (50% in water, 3.9 mL) was added to a flask containing 8 (74 mg, 0.20 mmol) at 0° C. Then saturated NaOH solution in MeOH (3.9 ml) was added at 0° C. DCM (3.9 mL) was added to aid substrate to dissolve. The mixture was heated at 25° C. for 18 hrs. Con. HCl was added to adjust pH to 7. It was concentrated in vacuo and the residue was purified by pre-HPLC to afford compound 001 (27 mg, yield: 38%) as a white solid. $^1$H NMR (500 MHz, DMSO) δ 10.96 (s, 1H), 9.00 (s, 1H), 8.63 (s, 1H), 8.35 (s, 1H), 8.29 (s, 1H), 7.39 (d, J=7.6 Hz, 2H), 7.28 (t, J=7.7 Hz, 2H), 7.17 (t, J=7.3 Hz, 1H), 2.73 (s, 2H), 2.23-1.88 (m, 6H). LCMS: m/z=349 (M+H)$^+$.

Example 2: Methods

Adult male C57/Bl6J mice received cisplatin intraperitoneally (i.p.) (2.3 mg/kg) daily for five days, followed by five days rest and a second round of five days of cisplatin treatment. Three days after the last dose of cisplatin, mice received the HDAC6 inhibitor, compound 001, a compound of Formula (I), i.p. for seven to fourteen days at 3 mg/kg or 10 mg/kg.

To quantify signs of cisplatin-induced pain, the von Frey test was used (see below) which measures the decrease in threshold to induce a withdrawal response to a mechanical stimulus (hyperalgesia, one of the characteristics of CIPN). To assess cisplatin-induced numbness, the adhesive removal test (ART) was used. The time it took for the mouse to have a behavioral response to the patch (i.e. shaking or attempted removal) was recorded as a measure of sensory deficit or numbness. To determine if behavioral changes were due to altered general activity or motor function, the locomotor activity (LMA) test and the rotarod test was used. For LMA mice were placed in an open-field testing cage and movement was measured for 5 minutes. For the rotarod, mice were trained for two days and then tested on the rotarod (with increasing speeds) for 5 minutes. Time on the rotarod was recorded.

Von Frey Testing:

Allodynic response to tactile stimulation is assessed using the Von Frey apparatus (Touch Test®).

The animal is placed in an enclosure and positioned on a metal mesh surface, but allowed to move freely. The animals' cabins are covered with red cellophane to diminish environmental disturbances. The test begins after a cessation of exploratory behavior. The set of Von Frey monofilaments provide an approximate logarithmic scale of actual force and a linear scale of perceived intensity.

The operating principle: when the tip of a fiber of given length and diameter is pressed against the skin at right angles, the force of application increases as long as the researcher continues to advance the probe until the fiber bends. After the fiber bends, the probe continues to advance, causing the fiber to bend more, but without additional force being applied.

Rodents exhibit a paw withdrawal reflex when the paw is unexpectedly touched. The Touch Test™ Sensory Evaluator can be used on the plantar surfaces of the rat's foot. The animal indicates sensation by pulling back its paw. The minimal force needed to elevate the withdrawal reflex is considered/designated as the value of reference. In order to achieve paw withdrawal, the pressure applied is sometimes greater than 60 g, often requiring the researcher to apply enough pressure with the Von Frey filament to actually lift the paw of the naive animal. Decreases in force needed to induce withdrawal are indicative of hyperalgesia, as the force applied is a non-painful stimulus under normal conditions.

For quantification of astrocyte and microglia activation, lumbar spinal cords were collected on day 22. This collection day was after completion of cisplatin treatment and 3 injections of compound 001. Mice showed recovery from cisplatin-induced mechanical hyperalgesia at this time. Spinal cords were processed and stained with antibodies specific for GFAP and Iba-1. Images were captured under blinded conditions from the lumbar dorsal horn using a Leica SPE confocal microscope (Leica Microsystems, Buffalo Grove, Ill.).

Animals.

Adult male C57BL/6J mice were housed at the Texas A&M Health Science Center Program for Animal Resources or the University of Texas M.D. Anderson Cancer Center animal facility. Mice were housed on a regular 12 h light/dark cycle with free access to food and water. All procedures were consistent with the National Institute of Health Guidelines for the Care and Use of Laboratory Animals and the Ethical Issues of the International Association for the Study of Pain (Zimmermann M. Ethical guidelines for investigations of experimental pain in conscious animals. *Pain*. 1983; 16(2):109-10) and were approved by the local Institution for Animal Care and Use Committee (IACUC).

Drug Administration.

Cisplatin (TEVA Pharmaceuticals, North Wales, Pa.) was diluted in sterile saline and administered intraperitoneally (i.p.) at a dose of 2.3 mg/kg daily for 5 days, followed by 5 days of rest, and a second round of 5 doses for a total cumulative dose of 23 mg/kg cisplatin. It was shown that this dosing schedule induces mechanical hyperalgesia in mice (Qi-Liang Mao-Ying A K, et al. The anti-diabetic drug metformin protects against chemotherapy-induced peripheral neuropathy in a mouse model. *Clinical Cancer Research*. 2014; Krukowski K, et al. Prevention of chemotherapy-induced peripheral neuropathy by the small-molecule inhibitor pifithrin-mu. *Pain*. 2015; 156(11):2184-92). HDAC6 inhibitor, compound 001, (Acetylon Pharmaceuticals, Boston, Mass.) was dissolved in 20% 2-hydroxypropyl-B-cyclodextrin+0.5% hydroxypropyl methylcellulose (Sigma-Aldrich, St. Louis, Mo.) in water and administered i.p. at a dose of 10 mg/kg or 3 mg/kg.

Von Frey Test for Mechanical Hyperalgesia

Mechanical hyperalgesia was measured as the hind paw withdrawal response to von Frey hair stimulation using the up-and-down method as described previously (Qi-Liang Mao-Ying A K, et al. The anti-diabetic drug metformin protects against chemotherapy-induced peripheral neuropathy in a mouse model. *Clinical Cancer Research*. 2014; Krukowski K, et al. Prevention of chemotherapy-induced peripheral neuropathy by the small-molecule inhibitor pifithrin-mu. *Pain*. 2015; 156(11):2184-92; Wang H, et al. GRK2 in sensory neurons regulates epinephrine-induced signalling and duration of mechanical hyperalgesia. *Pain*. 2011; 152(7):1649-58). Mice were placed in a plastic cage ($10 \times 10 \times 13$ cm$^3$) with a mesh floor for 30 min prior to testing. Subsequently, a series of von Frey hairs (0.02, 0.07, 0.16, 0.4, 0.6, 1.0 and 1.4 g) (Stoelting, Wood Dale, Ill., USA) were applied perpendicular to the mid-plantar surface of the hind paw. A trial began with the application of the 0.16 g hair. A positive response was defined as a clear paw withdrawal or shaking. Whenever a positive response occurred, the next lower hair was applied, and whenever a negative response occurred, the next higher hair was applied. The testing consisted of five stimuli after the first change in response occurred, and the pattern of response was converted to a 50% von Frey threshold using the method described previously (Chaplan S R, et al. Quantitative assessment of tactile allodynia in the rat paw. *J Neurosci Methods*. 1994; 53(1):55-63) by an investigator blinded to treatment until the end of the experiment.

Adhesive Removal Test (ART) for Numbness

To examine numbness, a modification of the adhesive removal test (Bouet V, et al. The adhesive removal test: a sensitive method to assess sensorimotor deficits in mice. *Nat. Protoc.* 2009; 4(10):1560-4) as described was used (Qi-Liang Mao-Ying A K, et al. The anti-diabetic drug metformin protects against chemotherapy-induced peripheral neuropathy in a mouse model. *Clinical Cancer Research*. 2014). Mice were habituated to a testing cage ($20 \times 20 \times 13$ cm$^3$) for 5 minutes prior to testing. A round adhesive patch (3/16" Teeny Touch-Spots, USA Scientific INC.) was placed on the plantar surface of the hind paws and the mouse was placed back in the testing cage. The time it took for the mouse to display a behavioral response to the patch (i.e. shaking or attempted removal) was recorded. A maximal testing time of 15 minutes was used.

Conditioned Place Preference Test for Spontaneous Pain

Spontaneous pain was tested using a conditioning paradigm with retigabine as the conditioned stimulus that was originally described in a rat model (Yang Q, et al. Persistent pain after spinal cord injury is maintained by primary afferent activity. *The Journal of Neuroscience*. 2014; 34(32): 10765-9; Ahmed B, et al. Recent changes in practice of elective percutaneous coronary intervention for stable angina. *Circ. Cardiovasc. Qual. Outcomes*. 2011; 4(3):300-5.). Retigabine is a common local anesthetic with a rapid onset of action but only brief duration (45-60 min). The dosage used in this study has been previously demonstrated to be effective in briefly relieving pain in models of neuropathic and inflammatory pain (Yang Q, et al. Persistent pain after spinal cord injury is maintained by primary afferent activity. *The Journal of Neuroscience*. 2014; 34(32):10765-9; Blackburn-Munro G, and Jensen B S. The anticonvulsant retigabine attenuates nociceptive behaviours in rat models of persistent and neuropathic pain. *Eur. J. Pharmacol.* 2003; 460(2-3):109-16; Xu W, et al. Activation of voltage-gated KCNQ/Kv7 channels by anticonvulsant retigabine attenuates mechanical allodynia of inflammatory temporomandibular joint in rats. *Mol. Pain*. 2010; 6(49); Passmore G M, et al. KCNQ/M currents in sensory neurons: significance for pain therapy. *The Journal of Neuroscience,* 2003; 23(18): 7227-36).

Briefly, during pre-conditioning, mice were allowed to freely explore for 15 min the CPP apparatus. The CPP apparatus consisted of 2 chambers (18×20 cm, one dark, one white) connected by a 15 cm hallway (Stoelting, Wood Dale, Ill.). The time spent in the light chamber was recorded. During the conditioning phase, saline was injected intraperitoneally in the morning and the mice were then kept in the dark chamber for 20 min. Three hours later, the analgesic retigabine (#R-100, Alomone laboratory, Jerusalem, Israel) was and the mice were immediately placed in the light chamber for 20 min. Conditioning was repeated for four consecutive days. The following day the mice did not receive any injections but were allowed to freely explore both chambers of the apparatus for 15 min. A mouse experiencing pain relieve by retigabine should show an increase in time spent in the light chamber that was paired with retigabine as compared to the pre-conditioning phase.
Immunofluorescence Staining For quantification of IENFs, biopsies from the plantar surface of the hind paws were collected after 3 doses or 11 doses of compound 001 or vehicle and processed as described previously (Qi-Liang Mao-Ying A K, et al. The anti-diabetic drug metformin protects against chemotherapy-induced peripheral neuropathy in a mouse model. *Clinical Cancer Research.* 2014); Krukowski K, et al. Prevention of chemotherapy-induced peripheral neuropathy by the small-molecule inhibitor pifithrin-mu. *Pain.* 2015; 156(11):2184-92). In brief, biopsies were fixed in Zamboni's fixative, cryoprotected in 20% sucrose and then frozen in Optimal Cutting Temperature compound (Sakura Finetek USA, Inc., Torrance, Calif.). 25-am frozen sections were incubated with antibodies against the pan neuronal marker PGP9.5 (Rabbit; AbD Serotec, Oxford, United Kingdom) and Collagen IV (Goat; Southern Biotech, Birmingham, Ala.) followed by Alexa-594 donkey anti-rabbit (Life Technologies, Carlsbad, Calif.) and Alexa-488 donkey anti-goat (Invitrogen, Grand Island, N.Y.). Three randomly chosen sections from each mouse were imaged and quantified under a Leica SPE confocal microscope (Leica Microsystems, Buffalo Grove, Ill.). Nerve fibers that crossed the collagen-stained dermal/epidermal junction into the epidermis were counted and IENF density was determined as the total number of fibers/length of epidermis (IENFs/mm).

For assessing astrocyte activation, paraformaldehyde fixed frozen 6 m sections of lumbar spinal cord (L1-L6) were incubated with an antibody against glial fibrillary acidic protein (GFAP) (Rabbit; Abcam, Cambridge, Mass.) followed by Alexa-594-goat anti-rabbit IgG (Life Technologies, Carlsbad, Calif.) as described (Zhang H, et al. Evidence that spinal astrocytes but not microglia contribute to the pathogenesis of Paclitaxel-induced painful neuropathy. *J. Pain,* 2012; 13(3):293-303). Images were captured using a Leica SPE confocal microscope (Leica Microsystems, Buffalo Grove, Ill.). GFAP staining intensity was quantified using Image J software for percent positive GFAP staining in which intensity thresholds were maintained between samples. All immunofluorescence analysis were done by an experimenter blinded to the treatment groups.
Mitochondrial Bioenergetics Analysis.

Tibial nerves were collected on experimental day 30, when the mice have received 2 rounds of cisplatin treatment and 11 injections of compound 001. Tissues were placed into islet capture XF24 microplate (Seahorse Bioscience, North Billerica, Mass.) in XF media with the addition of 5.5 mM glucose, 0.5 mM sodium pyruvate and 1 mM glutamine. Oligomycin (12 µM), FCCP (Carbonyl cyanide 4-(trifluoromethoxy)phenylhydrazone, 20 µM), and Rotenone/Antimycin A (20 µM each) (Sigma-Aldrich, St. Louis, Mo.) were injected sequentially during the assay. An assay cycle with a combination of 3-min mix, 3-min wait, and 4-min measure was repeated 4 times for baseline rates and after each port injection. After the respiratory measures, tissues were harvested and the oxygen consumption rate (OCR) values were normalized to the total protein content of each well. Basal respiration, ATP-linked respiration, proton leak, and maximal respiratory capacity were determined as described previously (Brand M D, and Nicholls D G. Assessing mitochondrial dysfunction in cells. *The Biochemical journal.* 2011; 435(2):297-312; Ma J, et al. Heat shock protein 70 is necessary to improve mitochondrial bioenergetics and reverse diabetic sensory neuropathy following KU-32 therapy. *The Journal of pharmacology and experimental therapeutics.* 2014; 348(2):281-92). Briefly, the initial measurements provide a measure of the basal OCR in the absence of respiratory chain poisons. The amount of basal OCR that is coupled to ATP production was determined by addition of the ATP synthase inhibitor oligomycin, which decreased the basal OCR. The magnitude of this decrease is representative of the ATP-linked OCR, whereas the residual OCR is attributable to uncoupled respiration (proton leak). Next, maximal respiratory capacity (MRC) was assessed by addition of the protonophore FCCP, which dissipates the mitochondrial membrane potential and promotes maximal OCR. Lastly, non-mitochondrial respiration was determined by the addition of rotenone and antimycin A, which inhibit the activities of mitochondrial respiratory chain complex I and complex III respectively.
Western Blot Analysis Tibial nerves retrieved from the XF24 assay plate were used for western blot analysis of levels of acetylated α-tubulin and mitochondrial proteins cytochrome c oxidase subunit IV (Cox IV), succinate dehydrogenase complex subunit A (SDHA) and voltage-dependent anion channel (VDAC). Tissues were homogenized in RIPA buffer (50 mM Tris-HCl, pH 7.5, 500 mM NaCl, 2.5 mM $MgCl_2$, 1% NP-40, 10% glycerol) containing proteinase inhibitors by sonication and 10 g of protein was separated by SDS/PAGE and transferred to PVDF membrane for immunoblot analyses. The membranes were blocked with 5% non-fat dry milk in PBST (phosphate-buffered saline containing 0.1% Tween 20) and probed with primary antibodies recognizing acetylated lysine (Rabbit monoclonal; Abcam, Cambridge, United Kingdom), α-tubulin (Rabbit polyclonal; Cell Signaling Technology, Danvers, Mass.), Cox IV (Mouse monoclonal; Life Technologies, Carlsbad, Calif.), SDHA (Rabbit polyclonal; Cell Signaling Technology, Danvers, Mass.) and VDAC (Rabbit polyclonal; Cell Signaling Technology, Danvers, Mass.) followed by HRP-conjugated anti-mouse, anti-rabbit, or anti-β-actin antibodies (Jackson Laboratory, Bar Harbor, Me.). Immunoreactivity for each protein was visualized using a chemiluminescence detection kit (GE Healthcare Life Sciences, Little Chalfont, United Kingdom). The images were acquired using ImageQuant LAS 4000 (GE Healthcare Life Sciences, Little Chalfont, United Kingdom) and densitometrically analyzed using Image J software.
Mitochondrial Movement in Cultured DRG Neurons.

DRG neurons (Lonza) were cultured for 5-7 days before the mitochondrial transport assay. 24 hrs prior to chemotherapy treatment cells were infected with Bacmam 2.0, which labeled mitochondria with GFP. Cells were treated with cisplatin (20-80 µM)+/−compound 001 (100 nM) for 3 hours. Imaging was performed using Zeiss 3i system. Time lapse images were acquired every 2 seconds over the course of 2 min. Image analysis was performed using Fiji and Multiple Kymograph plugin.

Figure 1A:
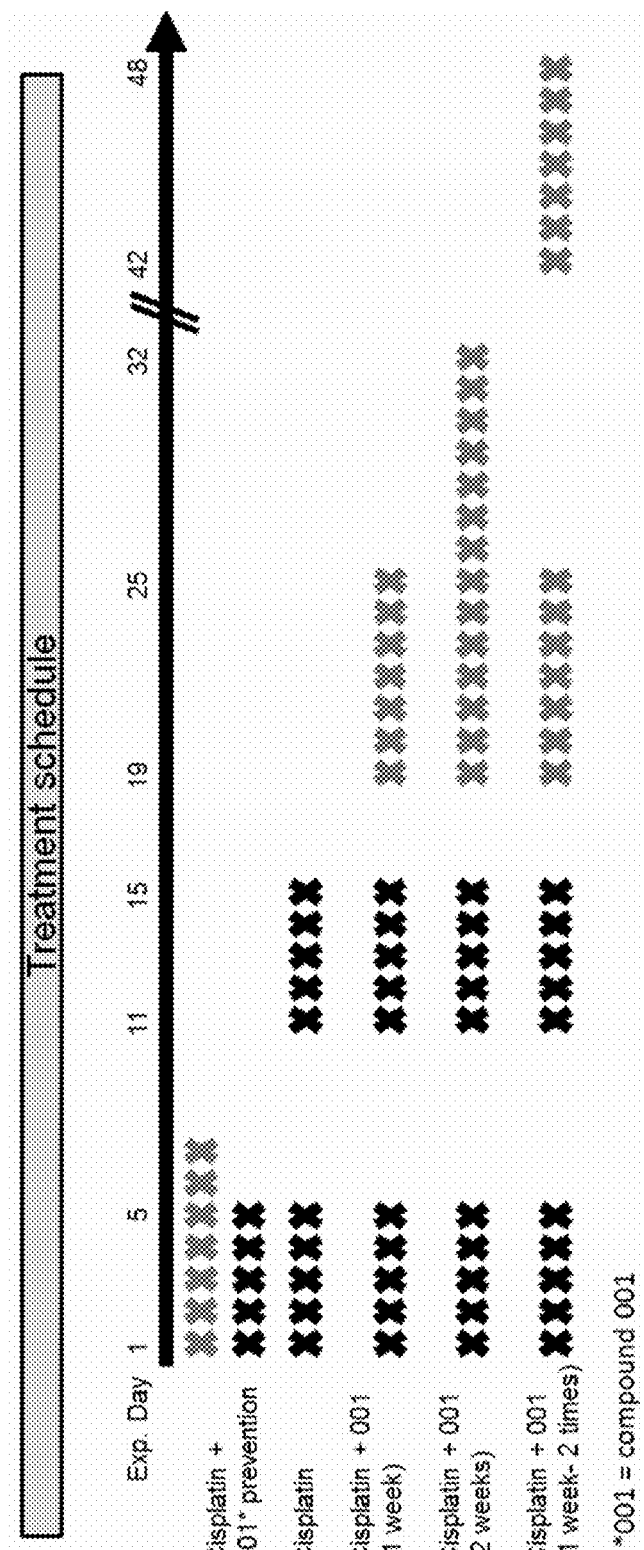
FIG. 1A shows cisplatin and compound 001 dosing schemes. All reagents were administered intraperitoneally (i.p.). Black X denotes cisplatin treatment (2.3 mg/kg); Gray X denotes compound 001 treatment.
Figure 1B:
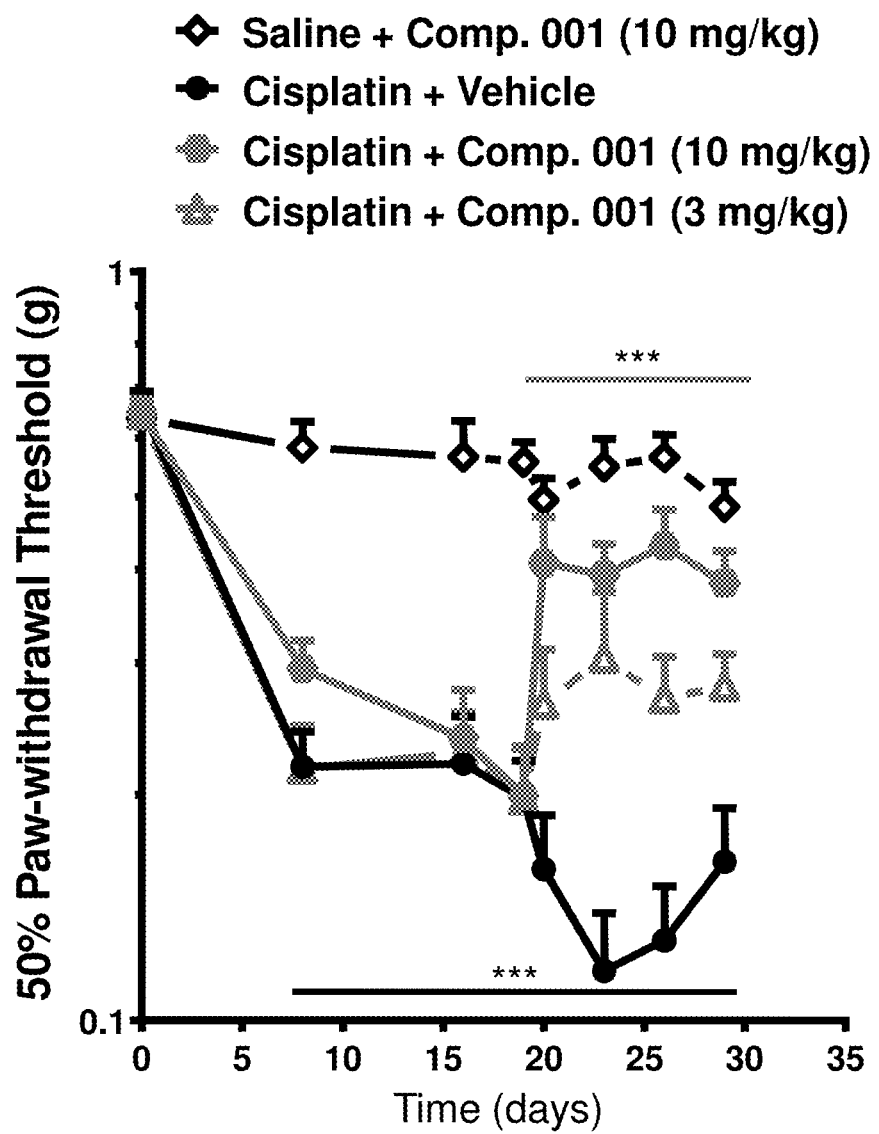
FIG. 1B shows that compound 001 treats mechanical hyperalgesia induced by cisplatin. Mice were administered with two rounds of cisplatin treatment; three days after the last cisplatin dose mice received compound 001 (10 mg/kg or 3 mg/kg) for 7 days (see dosing schedule in FIG. 1A). Two-way repeated measured ANOVA revealed a main effect of time ($p<0.01$), group ($p<0.01$), and a group by time interaction ($p<0.01$). Tukey post-hoc analysis was used to determine differences between groups at specified time points: *$p<0.001$ between Cisplatin+Vehicle vs. Saline+Vehicle; *$p<0.001$ between Cisplatin+compound 001 (10 mg/kg) vs. Cisplatin+Vehicle. n=10-12/group.
Figure 1C:
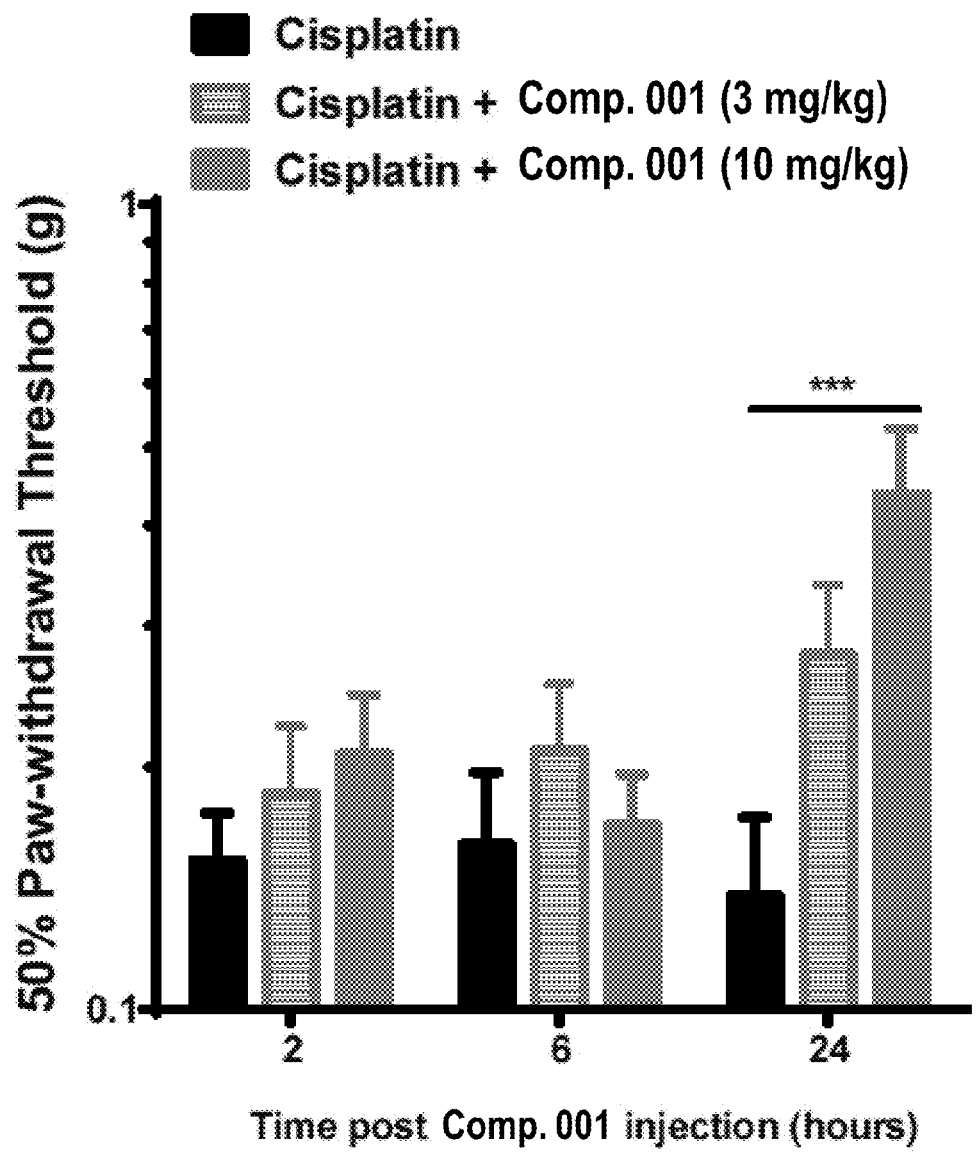
FIG. 1C shows the short term time course of the activity of compound 001. Mice were administered two rounds of cisplatin treatment as above. The effect of compound 001 developed slowly over time and was first detected 24 hours after the first dose of compound. Two-way repeated measured ANOVA showed a main effect of time ($p<0.05$) and a group by time interaction ($p<0.05$). Tukey post-hoc analysis for Cisplatin+compound 001 (10 mg/kg) vs. Cisplatin+Vehicle: ***$p<0.001$. n=6-8/group.
Figure 1D:
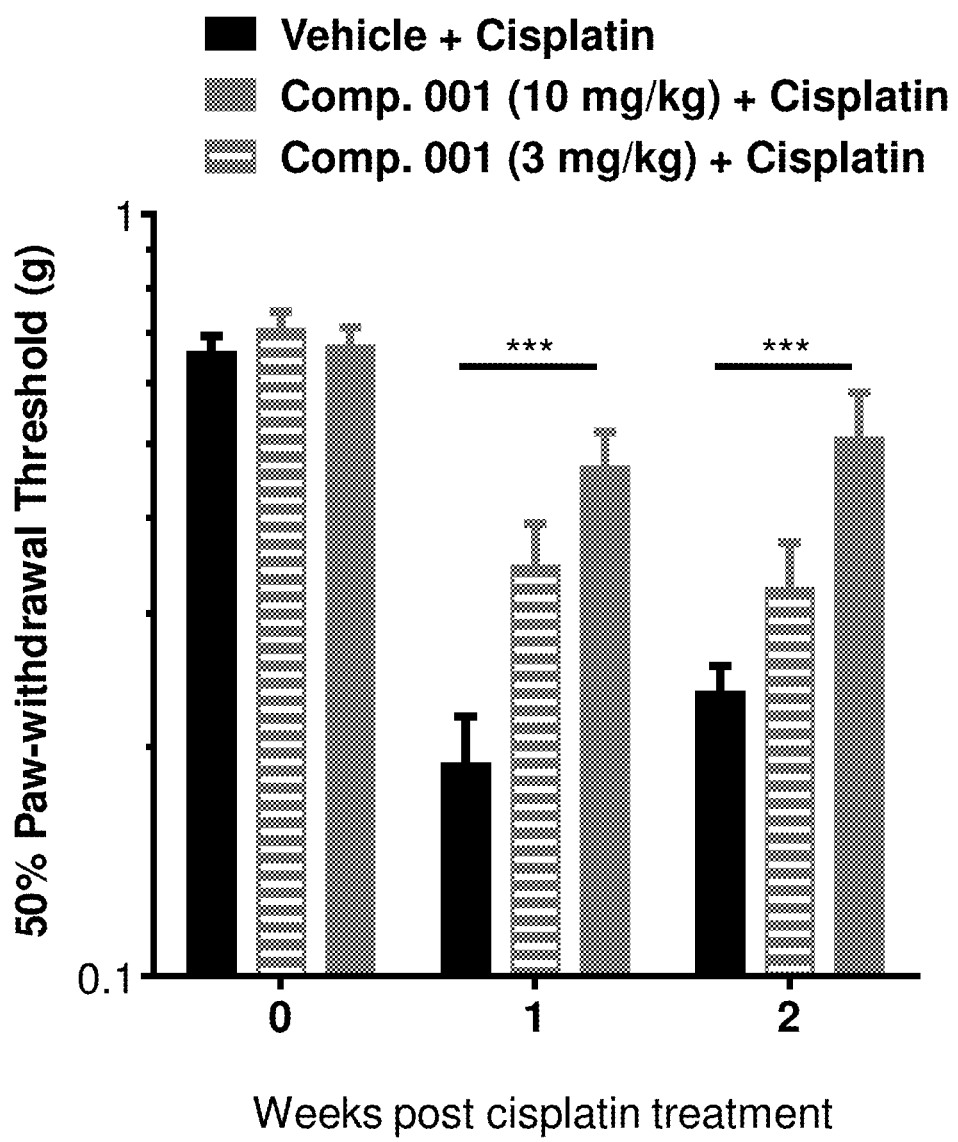
FIG. 1D shows that compound 001 prevents the development of mechanical hyperalgesia in mice treated with cisplatin. Compound 001 was administered one hour prior to each dose of cisplatin for one week. Mechanical hyperalgesia was measured for two weeks following the last cisplatin treatment. Two-way repeated measured ANOVA showed a main effect of time ($p<0.0001$), group ($p<0.03$), and a group by time interaction ($p<0.03$). Tukey post-hoc analysis for compound 001 (10 mg/kg)+Cisplatin vs. Vehicle+Cisplatin: ***$p<0.001$. n=6-8/group. Mice received cisplatin daily for five days. Compound 001 (10 mg/kg or 3 mg/kg) was administered (i.p.) one hour prior to each cisplatin injection and for two days after the last cisplatin injection.

Example 3: Compound 001 Prevents and Treats Mechanical Hyperalgesia Induced by Cisplatin To investigate whether the HDAC6 inhibitor compound 001 treats existing CIPN, mice received cisplatin (i.p.) (2.3 mg/kg) daily for five days, followed by five days rest and a second round of five days of cisplatin treatment (FIG. 1B) (Qi-Liang Mao-Ying A K, et al. The anti-diabetic drug metformin protects against chemotherapy-induced peripheral neuropathy in a mouse model. *Clinical Cancer Research.* 2014); Krukowski K, et al. Prevention of chemotherapy-induced peripheral neuropathy by the small-molecule inhibitor pifithrin-mu. *Pain.* 2015; 156(11):2184-92). Starting 3 days after the last dose of cisplatin, when mechanical hyperalgesia had already developed, mice received 7 daily doses of the HDAC6 inhibitor compound 001 (i.p. 3 mg/kg or 10 mg/kg) or vehicle. Treatment with 10 mg/kg compound 001 effectively relieved cisplatin-induced mechanical hyperalgesia while the lower dose of 3 mg/kg did not. (FIG. 1B). The effect of compound 001 on mechanical allodynia developed slowly over time and was first detected at 24 h after the first dose (FIG. 1C). Treatment with 10 mg/kg compound 001 alone did not alter mechanical sensitivity. A separate set of experiments found that compound 001 prevented the development of mechanical hyperalgesia when administered one hour prior to each dose of cisplatin (FIG. 1D).

Figure 2:
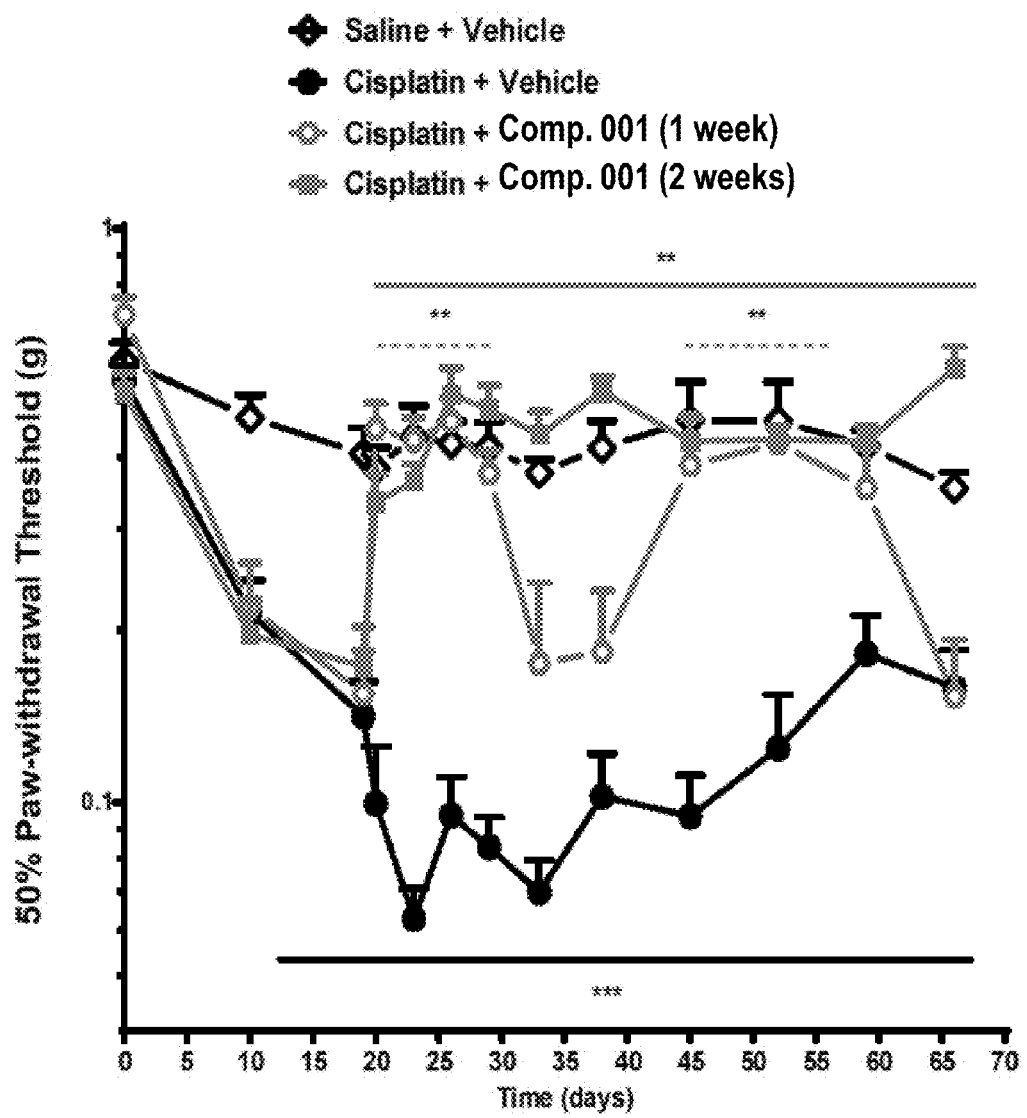
FIG. 2 shows that prolonged compound 001 treats mechanical hyperalgesia and induces sustained recovery. Mice were administered with two rounds of cisplatin treatment; three days after the last cisplatin dose mice received compound 001 (10 mg/kg) for 7 days followed by 7 days rest and then another 7 days following cisplatin treatment. Alternatively, mice received compound 001 (10 mg/kg) for 14 consecutive days (see dosing schedule in FIG. 1A). Mechanical hyperalgesia was measured using von Frey hairs and the 50% paw withdrawal threshold was calculated by the up-down method. Two-way repeated measured ANOVA revealed a main effect of time ($p<0.01$), a group effect ($p<0.01$), and a group by time interaction ($p<0.01$). Tukey post-hoc analysis was used to determine differences between groups at specified time points. *$p<0.001$ between Cisplatin+Vehicle vs. Saline+Vehicle; $p<0.01$ between Cisplatin+compound 001 vs. Cisplatin+Vehicle. n=6-14/group.

Example 4: Prolonged Compound 001 Treats Mechanical Hyperalgesia and Induces Sustained Recovery The beneficial effect of 7 daily doses (corresponding to the third line of FIG. 1A) of 10 mg/kg compound 001 on mechanical hyperalgesia was maintained until 4 days after the last dose (FIG. 2). Administration of a second round of 7 daily injections (corresponding to the fifth line of FIG. 1A) of compound 001 again transiently reversed cisplatin-induced mechanical hyperalgesia (FIG. 2). Notably, when Compound 001 was administered for two consecutive weeks (corresponding to the fourth line of FIG. 1A) starting 3 days after the last dose of cisplatin the complete and sustained recovery from mechanical hyperalgesia was observed (FIG. 2). The beneficial effect of the prolonged regimen of compound 001 was maintained until at least one month after the last dose of compound 001 (experiment termination). It is of note that at this time point mice treated with cisplatin alone still displayed marked mechanical hyperalgesia.

Example 5: Compound 001 Attenuates Cisplatin-Induced Numbness

Cisplatin-induced numbness was measured using adhesive removal task (ART) (Qi-Liang Mao-Ying A K, et al. The anti-diabetic drug metformin protects against chemotherapy-induced peripheral neuropathy in a mouse model. *Clinical Cancer Research.* 2014). In this test, a small sticker was placed on the hind paw and the time until the mouse displays a behavioral response to the sticker was recorded. Consistent with a previous study, cisplatin treatment prolonged the time to respond to the sticker in this test, indicating numbness.

Figure 3:
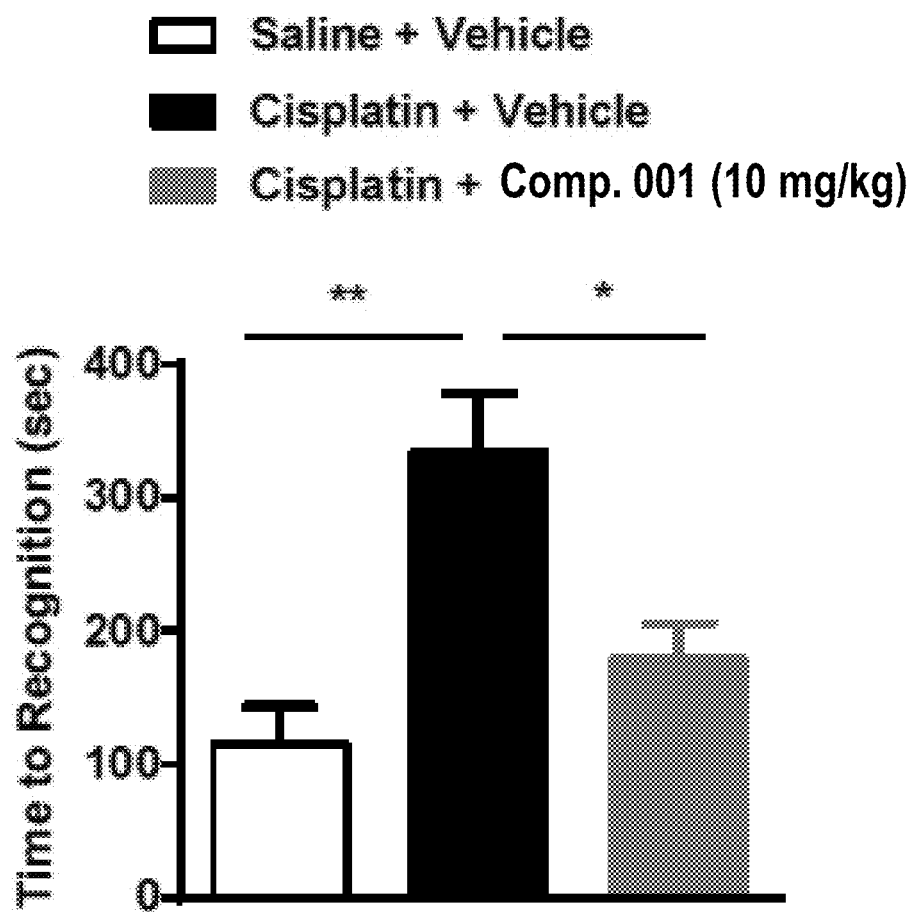
FIG. 3 shows that compound 001 attenuates cisplatin-induced numbness. Cisplatin-induced numbness was measured by the adhesive removal test (ART). Mice were tested in week 5 for cisplatin-induced numbness. Statistical analysis using one-way ANOVA revealed a significant difference between groups ($p<0.05$). Tukey post-hoc analysis was used to determine differences between groups. *$p<0.05$; **$p<01$. n=5-6/group.

Treatment with compound 001 starting after completion of the two rounds of cisplatin normalized the response time in this test, indicating reversal of the numbness. Stated alternatively, compound 001 treats cisplatin-induced numbness (FIG. 3).

Figure 4A:
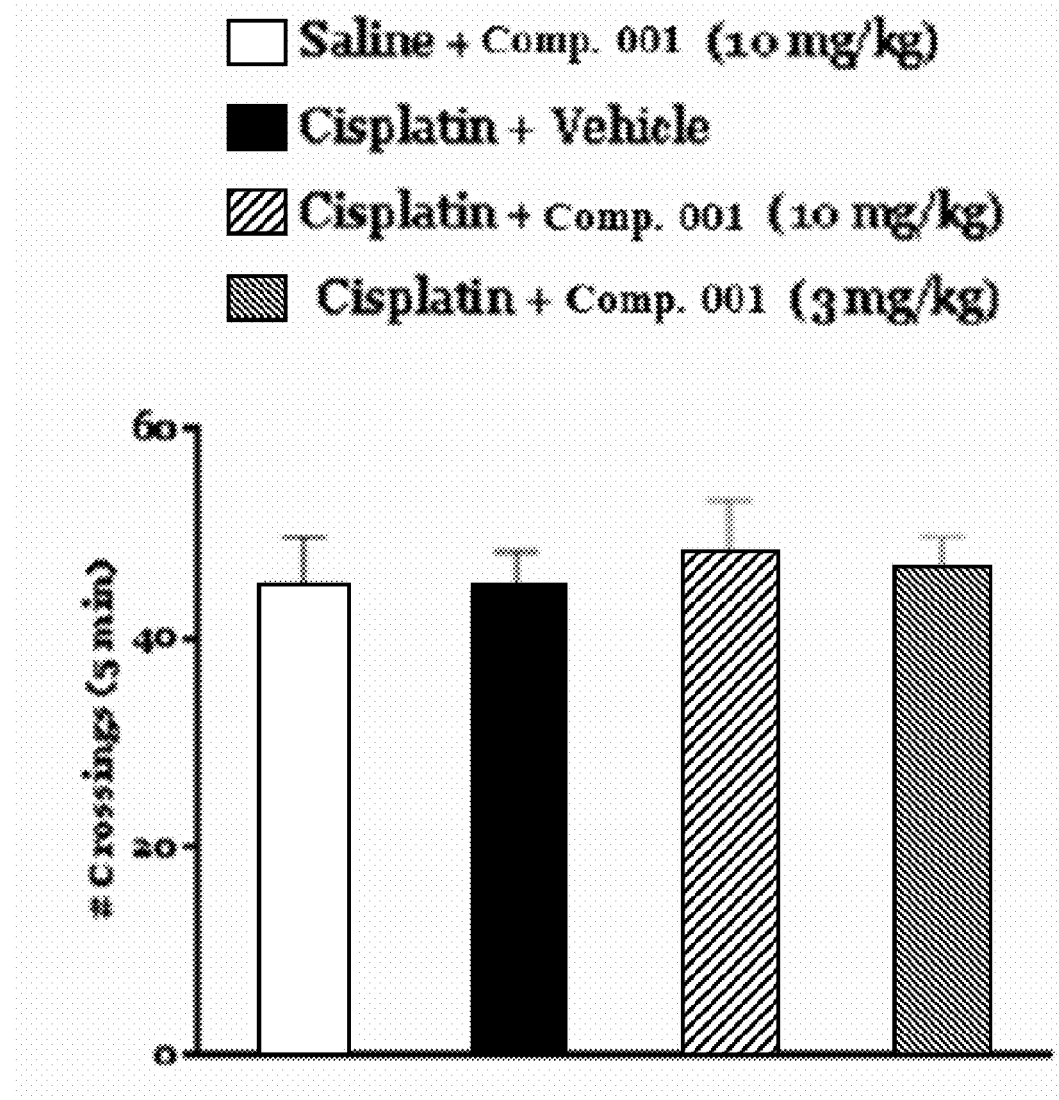
FIG. 4A and FIG. 4B show that compound 001 and cisplatin treatments do not change general activity or motor function. In the graphs, moving from left to right, the bars represent: saline+comp. 001 (10 mg/kg), cisplatin+vehicle, cisplatin+comp. 001 (10 mg/kg), and the far most right bar: cisplatin+comp. 001 (3 mg/kg).
Figure 4B:
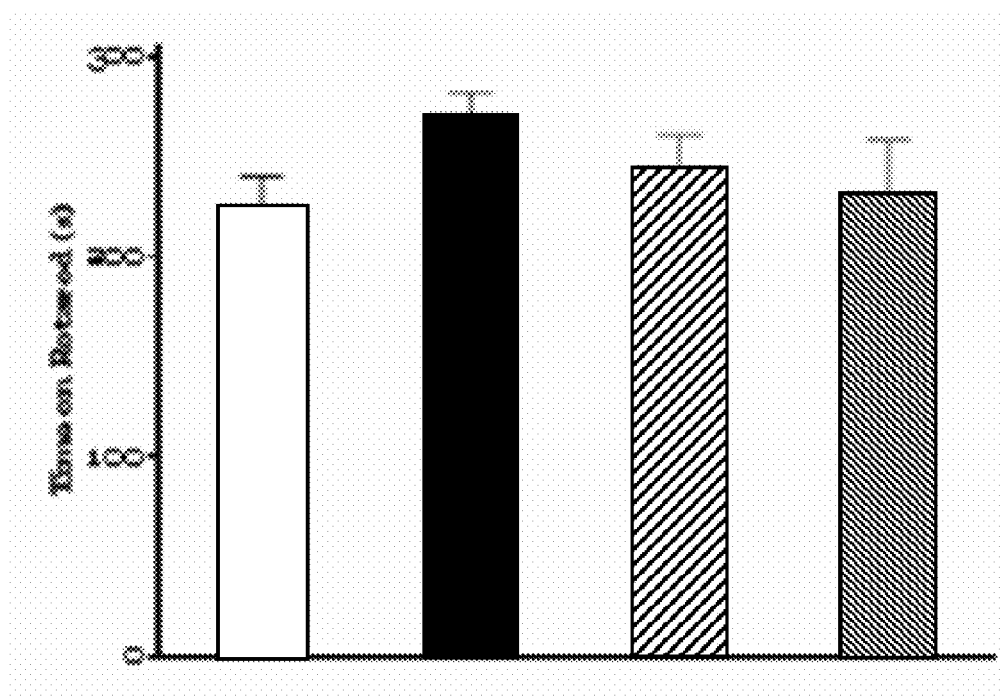

Example 6: Compound 001 and Cisplatin Treatment do not Change General Activity or Motor Function For the results shown in FIG. 4, general activity was measured using locomotor activity (LMA) (FIG. 4A) and motor function was measured using rotarod test (FIG. 4B). Cisplatin treatment alone or in combination with compound 001 had no effect on general activity or rotarod function n=5-6/group.

Figure 5:
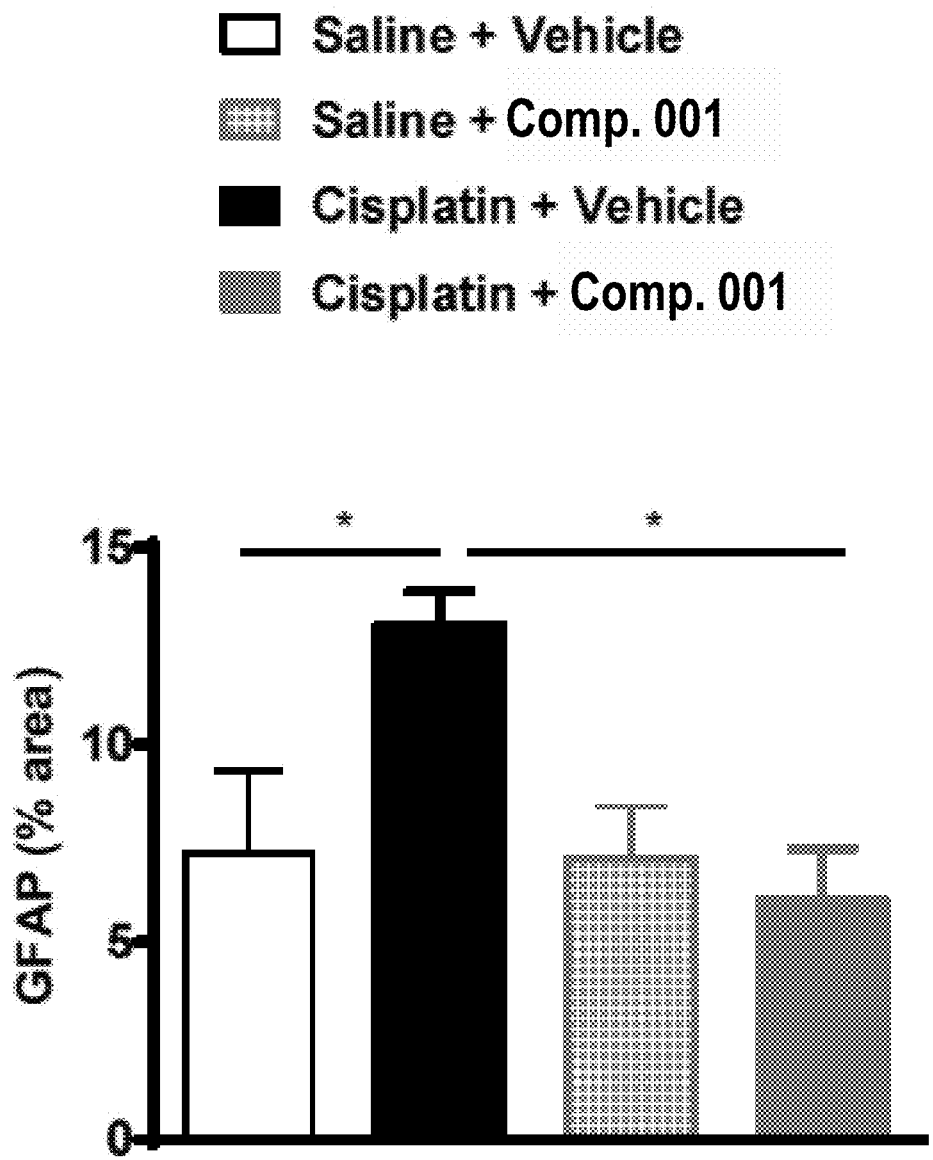
FIG. 5 shows that compound 001 decreases cisplatin-induced astrocyte activation in the spinal cord dorsal horn in mice. Mice were treated with two rounds of cisplatin followed by 3 doses of 10 mg/kg compound 001 treatment starting at day 4 after completion of cisplatin treatment. Lumbar spinal cord was stained for the astrocyte activation marker GFAP.

Example 7: Compound 001 Decreases Cisplatin-Induced Activation in the Spinal Cord Dorsal Horn CIPN is associated with spinal cord astrocyte activation as evidenced by an increase in GFAP expression (Zhang H, et al. Evidence that spinal astrocytes but not microglia contribute to the pathogenesis of Paclitaxel-induced painful neuropathy. *J Pain.* 2012; 13(3):293-303; Peters C M, et al. Intravenous paclitaxel administration in the rat induces a peripheral sensory neuropathy characterized by macrophage infiltration and injury to sensory neurons and their supporting cells. *Exp Neurol.* 2007; 203(1):42-54). Consistently, an increase in GFAP expression was detected in the dorsal horn of the spinal cord in cisplatin-treated mice. Compound 001 treatment normalized GFAP expression to levels of saline-treated animals (FIG. 5).

Example 8: Compound 001 Prevents Cisplatin-Induced Decreases in Mitochondrial Transport In Vitro (Effect of Cisplatin and Compound 001 on Mitochondrial Motility)

Tubulin acetylation status is a key regulator of neuronal mitochondrial transport (Chen S, et al. HDAC6 regulates mitochondrial transport in hippocampal neurons. *PLoS One.* 2010; 5(5):e10848). The effect of cipslatin and compound 001 on mitochondrial motility was examined in primary cultures of rat DRG neurons in which mitochondria were fluorescently labeled. Cultured DRG neurons were treated with cisplatin and compound 001 for 3 hours and mitochondrial movement in axons was measured using time-lapse imaging. Cisplatin-treatment decreased the percentage of moving mitochondria when compared to vehicle-treated cultures (FIG. 6). Co-administration of compound 001 (100 nM) prevented this cisplatin-induced decrease in mitochondrial transport.

Example 9: Effect of Cisplatin and Compound 001 on Peripheral Nerve Mitochondrial Function In Vivo To test whether compound 001 impacts mitochondrial function in vivo, the mitochondrial bioenergetics were assessed in tibial nerves of mice treated with two cycles of cisplatin followed by compound 001. Cisplatin-treatment significantly decreased mitochondrial respiration in tibial nerves (FIG. 7A); specifically, decreases were detected in basal respiration, ATP-linked respiration and proton leak as assessed after addition of oligomycin, and maximal respiration as assessed after addition of FCCP. Notably, treatment with compound 001 normalized all aspects of the cisplatin-induced decrease in mitochondrial respiration, indicating normalization of mitochondrial bioenergetics. The non-mitochondrial respiration was not altered in either cisplatin-treated or compound 001-treated mice. Compound 001 treatment alone did not have any effect on mitochondrial bioenergetics.

To determine whether the overall decrease in mitochondrial bioenergetics in response to cisplatin and the normalization by compound 001 was associated with changes in mitochondrial content in the distal nerves, Western blot analysis was performed for the mitochondrial proteins cytochrome c oxidase subunit IV (Cox IV), succinate dehydrogenase complex subunit A (SDHA) and voltage-dependent anion channel (VDAC). The level of Cox IV in the tibial nerves of cisplatin-treated mice was significantly reduced when compared to saline-treated mice. Moreover, treatment with compound 001 normalized Cox IV levels in the tibial nerve (FIG. 7B). Similar effects were observed when SDHA and VDAC were assessed (FIG. 7C). These findings indicate that inhibition of HDAC6 reversed cisplatin-induced reductions in mitochondrial bioenergetics, which is likely due to enhanced mitochondrial content in the distal nerve.

Example 10: HDAC6 Inhibition Treats Spontaneous Pain and Numbness Induced by Cisplatin Patients with CIPN do not only report hyperalgesia, but also spontaneous pain as well as numbness. Therefore, it was determined whether inhibition of HDAC6 also reverses spontaneous pain and numbness in the utilized mouse model. To measure spontaneous pain, a conditioned place preference (CPP) test with the nerve blocker retigabine as the conditioning stimulus was utilized (Yang Q, et al. Persistent pain after spinal cord injury is maintained by primary afferent activity. *The Journal of neuroscience: the official journal of the Society for Neuroscience.* 2014; 34(32):10765-9.). During the conditioning phase, mice received saline injections paired with exposure to a dark chamber and retigabine injections paired with exposure to a light chamber. On the test day the mice were allowed to freely explore both chambers and the change in time spent in the light chamber after conditioning is recorded. The results in FIG. 8 show that cisplatin-treated mice increased the time spent in the light chamber that was paired with retigabine, indicating ongoing pain. The saline-treated mice maintain a preference for the dark chamber. Mice that were treated with cisplatin followed by two weeks of daily compound 001 did not develop a preference for the retigabine-paired light chamber, indicating that these mice no longer experience pain. There were no group differences in time spent in the light chamber before conditioning.

Example 11: HDAC6 Inhibition Induces α-Tubulin Acetylation In Vivo

To determine whether compound 001 inhibits HDAC6-mediated protein de-acetylation in vivo, the effect of compound 001 on acetylation of α-tubulin was examined (Hubbert C, et al. HDAC6 is a microtubule-associated deacetylase. *Nature.* 2002; 417(6887):455-8). Tibial nerves were collected from mice treated with cisplatin followed by compound 001 or vehicle treatment. FIG. 9 shows that compound 001 treatment increased α-tubulin acetylation in both saline+compound 001 and cisplatin+compound 001 treated mice. Changes in tubulin acetylation in mice treated with cisplatin alone were not detected (FIG. 9).

Example 12: Effect of HDAC6 Inhibition on Intra-Epidermal Nerve Fiber Density Cisplatin-treatment is known to reduce the intra-epidermal nerve fiber (IENF) density in the plantar surface of the paw (Qi-Liang Mao-Ying A K, et al. The anti-diabetic drug metformin protects against chemotherapy-induced peripheral neuropathy in a mouse model. *Clinical Cancer Research.* 2014). It has been hypothesized that this reduction is due to mitochondrial damage as these peripheral nerve fibers represent bioenergetically demanding regions (Bennett G J, et al. Mitotoxicity in distal symmetrical sensory peripheral neuropathies. *Nat. Rev. Neurol.* 2014; 10(6):326-36). Consistent with a previous report (Qi-Liang Mao-Ying A K, et al. The anti-diabetic drug metformin protects against chemotherapy-induced peripheral neuropathy in a mouse model. *Clinical Cancer Research.* 2014), cisplatin-treatment reduced the IENF density. Remarkably, the prolonged regimen of compound 001 treatment completely reversed the cisplatin-induced loss of IENFs (FIG. 10). In contrast, short-term treatment with compound 001 did not have any effect on IENF density, indicating that prolonged treatment with compound 001 promoted restoration of IENF density rather than preventing the progression of IENF loss.

INCORPORATION BY REFERENCE

The contents of all references (including literature references, issued patents, published patent applications, and co-pending patent applications) cited throughout this application are hereby expressly incorporated herein in their entireties. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the invention described herein. Such equivalents are intended to be encompassed by the following claims.

We claim:

1. A method of alleviating numbness associated with cisplatin-induced peripheral neuropathy in a subject in need thereof comprising administering to the subject a therapeutically effective amount of a histone deacetylase 6 selective inhibitor, to thereby alleviate the numbness associated with the cisplatin-induced peripheral neuropathy.

2. The method of claim 1, wherein the histone deacetylase 6 selective inhibitor is compound 001:

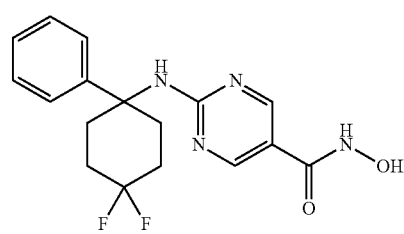

or a pharmaceutically acceptable salt thereof.

3. The method of claim 1, wherein the histone deacetylase 6 selective inhibitor is co-administered with cisplatin.

4. The method of claim 1, wherein the histone deacetylase 6 selective inhibitor is administered before or after administering cisplatin.

5. The method of claim 1, wherein the cisplatin-induced peripheral neuropathy exists in the subject prior to administering the histone deacetylase 6 selective inhibitor.

6. The method of claim 1, further comprising assessing numbness in the subject following treatment with the histone deacetylase 6 selective inhibitor.

* * * * *